(12) United States Patent
Nakayama

(10) Patent No.: US 11,317,882 B2
(45) Date of Patent: May 3, 2022

(54) RADIOGRAPHY SYSTEM, MEDICAL IMAGING SYSTEM, CONTROL METHOD, AND CONTROL PROGRAM

(71) Applicant: FUJIFILM CORPORATION, Tokyo (JP)

(72) Inventor: Hiroki Nakayama, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 139 days.

(21) Appl. No.: 16/777,862

(22) Filed: Jan. 30, 2020

(65) Prior Publication Data
US 2020/0253572 A1 Aug. 13, 2020

(30) Foreign Application Priority Data
Feb. 8, 2019 (JP) .............................. JP2019-022120

(51) Int. Cl.
*A61B 8/00* (2006.01)
*A61B 6/00* (2006.01)
(Continued)

(52) U.S. Cl.
CPC ............ *A61B 6/502* (2013.01); *A61B 6/0414* (2013.01); *A61B 6/06* (2013.01); *A61B 6/461* (2013.01); *A61B 6/54* (2013.01)

(58) Field of Classification Search
CPC ........... A61B 6/502; A61B 6/461; A61B 6/06; A61B 6/54; A61B 8/463; A61B 8/464;
(Continued)

(56) References Cited

U.S. PATENT DOCUMENTS 7,413,344 B2 * 8/2008 Qian ..................... G01N 23/04
378/206
2009/0225936 A1 9/2009 Kashiwagi et al.
(Continued)

FOREIGN PATENT DOCUMENTS

EP 2366333 A1 9/2011
JP 2009-207808 A 9/2009
(Continued)

OTHER PUBLICATIONS

Extended European Search Report dated Jun. 19, 2020, issued in corresponding EP Patent Application No. 20155289.0.
(Continued)

*Primary Examiner* — Don K Wong
(74) *Attorney, Agent, or Firm* — Solaris Intellectual Property Group, PLLC

(57) ABSTRACT

A radiography system includes: a mammography apparatus that includes a radiation source, a radiation detector, and a compression member which compresses a breast disposed between the radiation source and the radiation detector and captures a radiographic image of the breast in a compressed state using the radiation detector; and a control device including an acquisition unit that acquires region information indicating a region of an object of interest in the breast on the basis of the radiographic image captured by the mammography apparatus and a display control unit that performs control to display the region of the object of interest on the compression member, which continues to compress the breast from the capture of the radiographic image, so as to be recognizable on the basis of the region information acquired by the acquisition unit.

16 Claims, 16 Drawing Sheets

(51) Int. Cl.
*A61B 6/04* (2006.01)
*A61B 6/06* (2006.01)

(58) Field of Classification Search
CPC ......... A61B 8/465; A61B 8/466; A61B 8/469; A61B 8/0825; A61B 6/5217; A61B 8/461; A61B 8/14; G06T 7/0042; G06T 7/0051; G06T 2207/10116; G06T 2207/30068; G06T 2207/10132; G06T 2207/30204; G06K 9/4671; G05K 9/52
See application file for complete search history.

(56) References Cited

U.S. PATENT DOCUMENTS

| | | |
|---|---|---|
| 2010/0208037 A1 | 8/2010 | Sendai |
| 2011/0230759 A1 | 9/2011 | Muller |
| 2011/0295115 A1 | 12/2011 | Yarnall |
| 2012/0029344 A1 | 2/2012 | Nakayama |
| 2016/0110875 A1* | 4/2016 | Sugiyama ............. G06T 7/0012 382/131 |
| 2017/0128037 A1* | 5/2017 | Mori ...................... A61B 8/463 |
| 2017/0172531 A1 | 6/2017 | Sugiwama et al. |
| 2017/0281131 A1 | 10/2017 | Sendai |
| 2017/0290569 A1* | 10/2017 | Utsunomiya .......... A61B 8/466 |

FOREIGN PATENT DOCUMENTS

| | | |
|---|---|---|
| JP | 2009-240467 A | 10/2009 |
| JP | 2010-188003 A | 9/2010 |
| JP | 2010-253245 A | 11/2010 |
| JP | 2011-200655 A | 10/2011 |
| JP | 2017-113540 A | 6/2017 |
| JP | 2017-176509 A | 10/2017 |
| WO | 2006061357 A1 | 6/2006 |

OTHER PUBLICATIONS

English language translation of the following: Office action dated Dec. 14, 2021 from the JPO in a Japanese patent application No. 2019-022120 corresponding to the instant patent application. This office action translation is submitted now in order to supplement the understanding of the cited references which are being disclosed in the instant Information Disclosure Statement.

* cited by examiner

RADIOGRAPHY SYSTEM, MEDICAL IMAGING SYSTEM, CONTROL METHOD, AND CONTROL PROGRAM

CROSS-REFERENCE TO RELATED APPLICATION

This application claims priority, under 35 U.S.C. § 119, from Japanese Patent Application No. 2019-022120, filed Feb. 8, 2019, the disclosure of which is incorporated herein by reference in its entirety.

BACKGROUND

Technical Field

The present disclosure relates to a radiography system, a medical imaging system, a control method, and a non-transitory storage medium storing a control program.

Related Art

A radiography apparatus has been known which irradiates an object, such as the breast of a subject, with radiation emitted from a radiation source and detects the radiation transmitted through the object with a radiation detector to capture a radiographic image.

In addition, there is a technique that derives a mammary gland region of the breast from a radiographic image and displays the mammary gland region. For example, JP2017-113540A discloses a technique which displays a mammary gland region detected from the previous radiographic image on a compression member that compresses the breast in the current imaging in order to perform positioning with the previous capture of a radiographic image in a mammography apparatus, thereby supporting positioning in the current imaging.

As such, in a case in which compression by the compression member is released, in general, the compressed state of the breast in the previous compression before the decompression is different from the compressed state of the breast in re-compression after the decompression. In some cases, the developed state of the mammary gland (mammary gland region) varies depending on the compressed state of the breast. Therefore, in the technique described in JP2017-113540A, the displayed mammary gland region may be inappropriate.

SUMMARY

The present disclosure has been made in view of the above-mentioned problems and an object of the present disclosure is to provide a radiography system, a medical imaging system, a control method, and a non-transitory storage medium storing a control program that can appropriately display a mammary gland region of the breast in a compressed state on a compression member which compresses the breast.

In order to achieve the object, according to a first aspect of the present disclosure, there is provided a radiography system comprising: a mammography apparatus that includes a radiation source, a radiation detector, and a compression member which compresses a breast disposed between the radiation source and the radiation detector and captures a radiographic image of the breast in a compressed state using the radiation detector; and a control device including an acquisition unit that acquires region information indicating a region of an object of interest in the breast on the basis of the radiographic image captured by the mammography apparatus and a display control unit that performs control to display the region of the object of interest on the compression member, which continues to compress the breast from the capture of the radiographic image, so as to be recognizable on the basis of the region information acquired by the acquisition unit.

According to a second aspect of the present disclosure, in the radiography system according to the first aspect, the object of interest may be a mammary gland of the breast and the region of the object of interest may be a mammary gland region of the breast.

According to a third aspect of the present disclosure, in the radiography system according to the first or second aspect, the acquisition unit may derive the region of the object of interest on the basis of the radiographic image.

According to a fourth aspect of the present disclosure, the radiography system according to any one of the first to third aspects may further comprise a correction unit that corrects a size of a display region of the object of interest. The display control unit may perform control to display the region of the object of interest in the display region corrected by the correction unit.

According to a fifth aspect of the present disclosure, in the radiography system according to the fourth aspect, the correction unit may correct the size of the display region of the object of interest on the basis of a distance between the radiation source and the radiation detector and a distance between the object of interest and the radiation detector.

According to a sixth aspect of the present disclosure, in the radiography system according to the fourth aspect, the correction unit may correct the size of the display region of the object of interest on the basis of a distance between the radiation source and the radiation detector and a thickness of the breast.

According to a seventh aspect of the present disclosure, in the radiography system according to the fourth aspect, the correction unit may correct the size of the display region of the object of interest on the basis of a distance between the radiation source and the radiation detector and a distance between the compression member and the radiation detector.

According to an eighth aspect of the present disclosure, the radiography system according to any one of the first to seventh aspects may further comprise a visible light source that emits visible light and a limitation unit that limits an irradiation region of the visible light under the control of the display control unit.

According to a ninth aspect of the present disclosure, in the radiography system according to the eighth aspect, the mammography apparatus may further comprise a collimator that limits an irradiation field of radiation emitted from the radiation source and the limitation unit may limit the irradiation region of the visible light using the collimator.

According to a tenth aspect of the present disclosure, in the radiography system according to the eighth or ninth aspect, the display control unit may perform control for the limitation unit such that the irradiation region is matched with the region of the object of interest on the basis of a position of the visible light source and an irradiation angle of the visible light.

According to an eleventh aspect of the present disclosure, in the radiography system according to any one of the first to seventh aspects, the mammography apparatus may display an irradiation field of radiation emitted from the radiation source with visible light and the display control unit may perform control to display the region of the object of interest with visible light that is different from the visible light for displaying the irradiation field in any one of hue, brightness, or saturation.

According to a twelfth aspect of the present disclosure, in the radiography system according to any one of the first to eleventh aspects, in a case in which there are a plurality of regions of the object of interest, the display control unit may perform control to sequentially display the plurality of regions of the object of interest.

According to a thirteenth aspect of the present disclosure, in the radiography system according to any one of the first to twelfth aspects, the display control unit may further perform control to display the radiographic image captured by the mammography apparatus on the compression member.

In order to achieve the object, according to a fourteenth aspect of the present disclosure, there is provided a medical imaging system comprising: the radiography system according to any one of the first to thirteenth aspects; and an ultrasonography apparatus that captures an ultrasound image of the breast compressed by the compression member of the mammography apparatus in the radiography system.

In order to achieve the object, according to a fifteenth aspect of the present disclosure, there is provided a control method performed by a computer, comprising: acquiring region information indicating a region of an object of interest in a breast on the basis of a radiographic image captured by a mammography apparatus that includes a radiation source, a radiation detector, and a compression member which compresses the breast disposed between the radiation source and the radiation detector and captures the radiographic image of the breast in a compressed state using the radiation detector; and performing control to display the region of the object of interest on the compression member, which continues to compress the breast from the capture of the radiographic image, so as to be recognizable on the basis of the acquired region information.

In order to achieve the object, according to a sixteenth aspect of the present disclosure, there is provided a non-transitory storage medium storing a program that causes a computer to perform a control processing, the control processing including: acquiring region information indicating a region of an object of interest in a breast on the basis of a radiographic image captured by a mammography apparatus that includes a radiation source, a radiation detector, and a compression member which compresses the breast disposed between the radiation source and the radiation detector and captures the radiographic image of the breast in a compressed state using the radiation detector; and performing control to display the region of the object of interest on the compression member, which continues to compress the breast from the capture of the radiographic image, so as to be recognizable on the basis of the acquired region information.

A radiography system according to the present disclosure includes a processor. The processor acquires region information indicating a region of an object of interest in a breast on the basis of a radiographic image captured by a mammography apparatus that includes a radiation source, a radiation detector, and a compression member which compresses the breast disposed between the radiation source and the radiation detector and captures the radiographic image of the breast in a compressed state using the radiation detector and performs control to display the region of the object of interest on the compression member, which continues to compress the breast from the capture of the radiographic image, so as to be recognizable on the basis of the acquired region information.

According to the present disclosure, it is possible to appropriately display a mammary gland region of the breast in a compressed state on a compression member that compresses the breast.

DETAILED DESCRIPTION

Hereinafter, embodiments of the invention will be described in detail with reference to the drawings. Each of the embodiments does not limit the invention. In each of the embodiments, for example, a case in which an object of interest of the present disclosure is the mammary gland will be described.

First Embodiment

Figure 1:
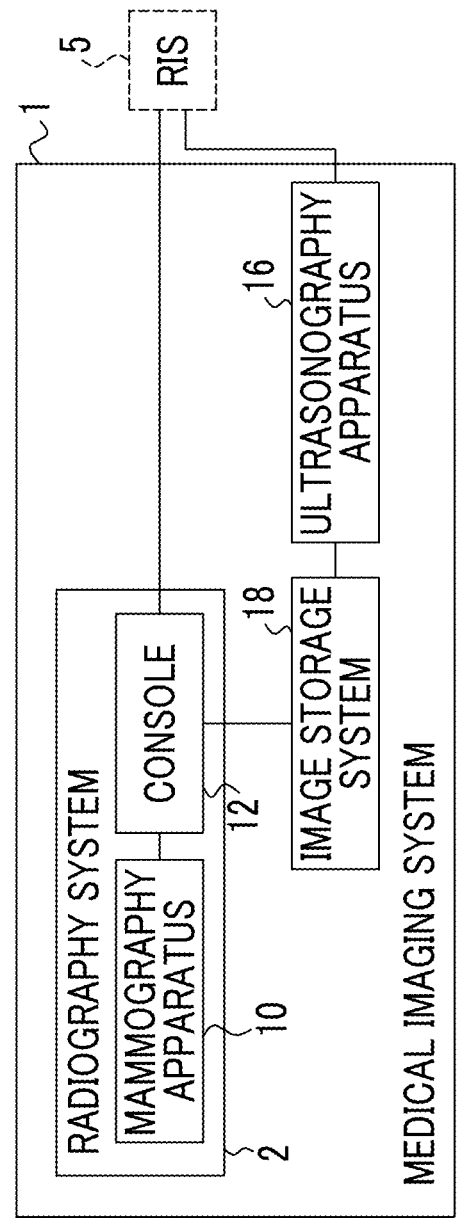
FIG. 1 is a diagram schematically illustrating an example of the overall configuration of a medical imaging system according to a first embodiment.

First, an example of the entire configuration of a medical imaging system according to this embodiment will be described. FIG. 1 is a diagram illustrating an example of the overall configuration of a medical imaging system 1 according to this embodiment.

As illustrated in FIG. 1, the medical imaging system 1 according to this embodiment comprises a radiography system 2, an ultrasonography apparatus 16, and an image storage system 18.

Figure 2:
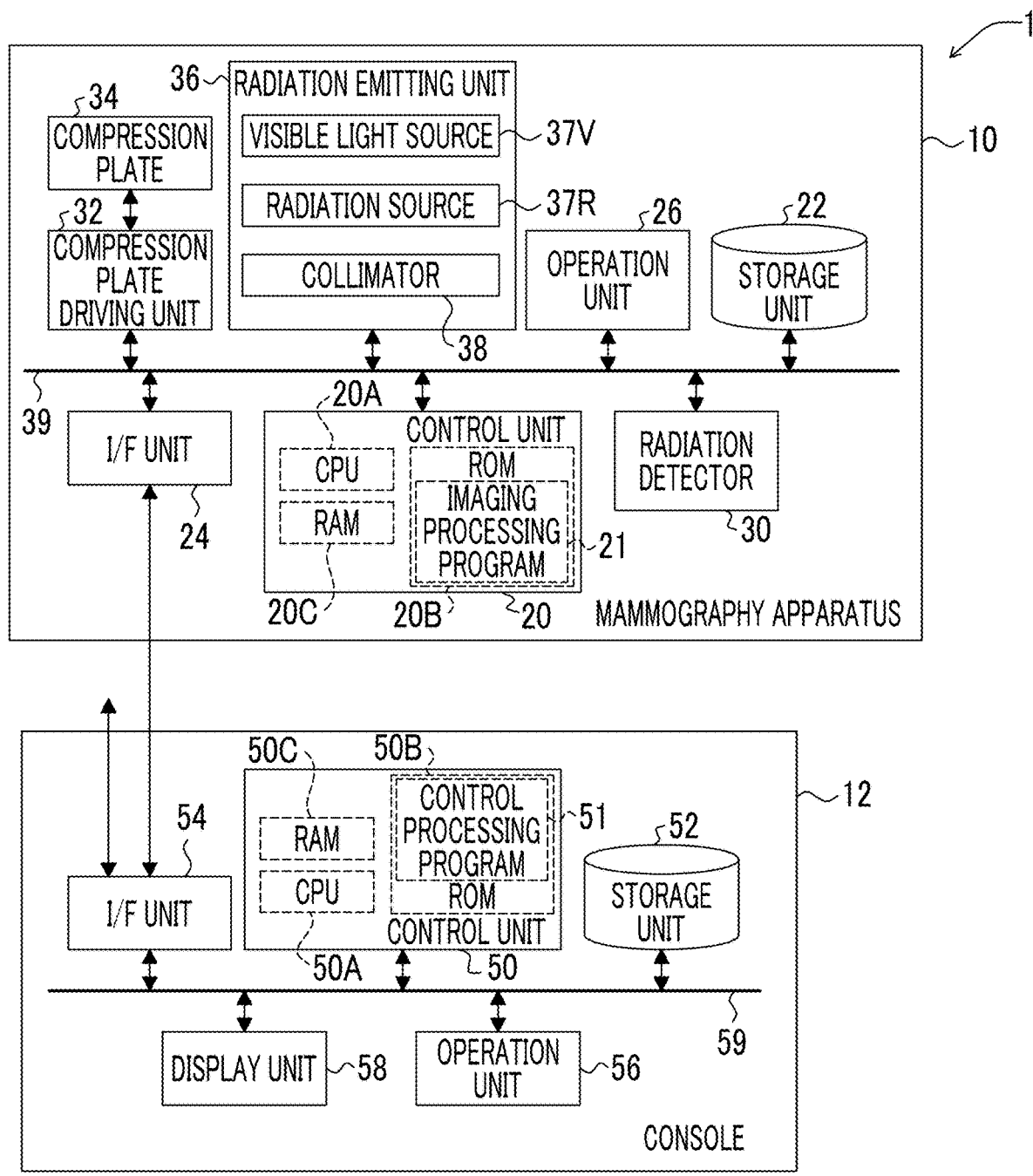
FIG. 2 is a block diagram illustrating an example of the configuration of a console and a mammography apparatus according to the first embodiment.
Figure 3:
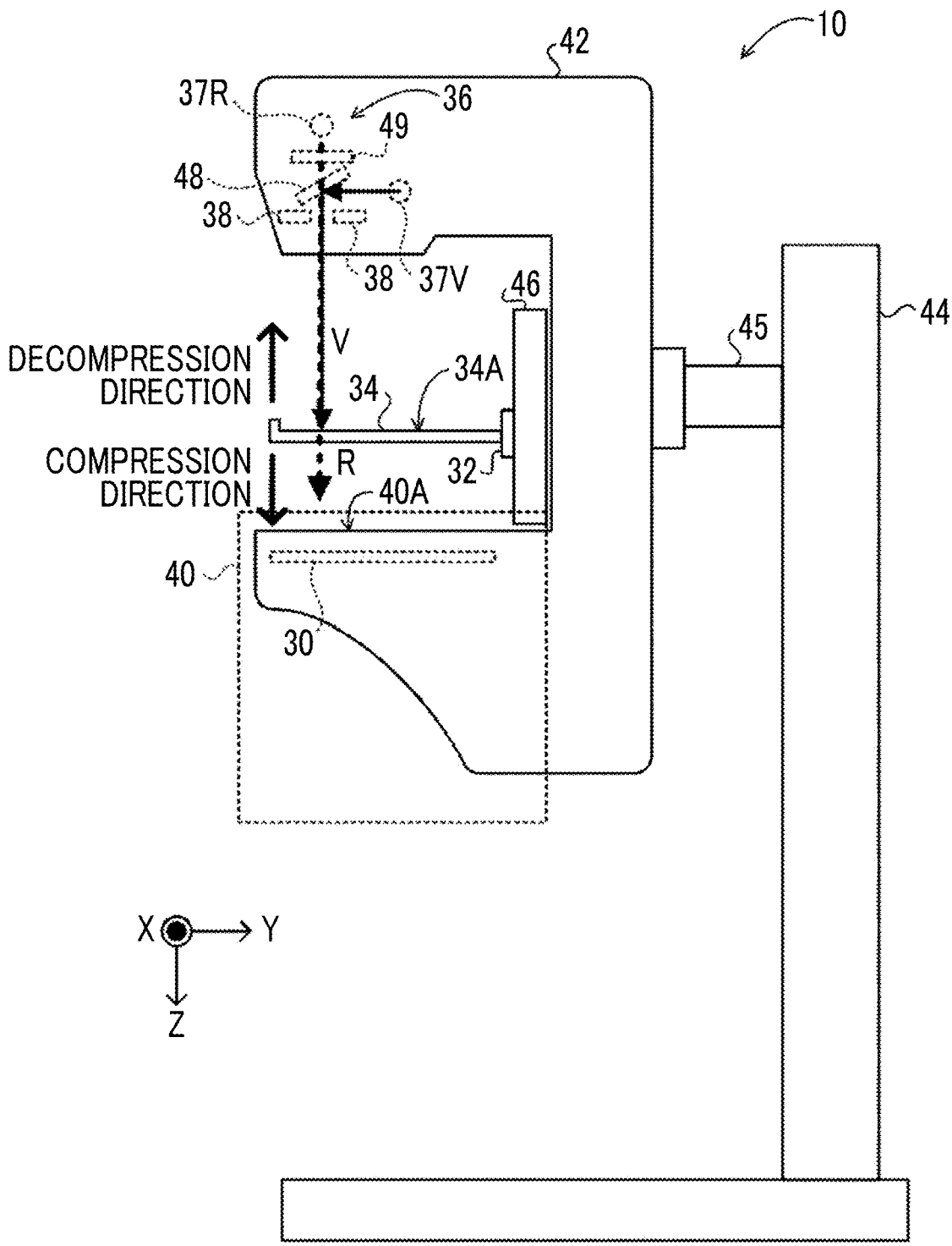
FIG. 3 is a side view illustrating an example of the outward appearance of the mammography apparatus according to the first embodiment.

First, the configuration of the radiography system 2 will be described. The radiography system 2 includes a mammography apparatus 10 and a console 12. FIG. 2 is a block diagram illustrating an example of the configuration of the mammography apparatus 10 and the console 12. FIG. 3 is a side view illustrating an example of the outward appearance of the mammography apparatus 10 according to this embodiment.

The mammography apparatus 10 according to this embodiment irradiates the breast of a subject as an object with radiation R (for example, X-rays) to capture a radiographic image of the breast. In addition, the mammography apparatus 10 may be an apparatus that captures the image of the breast of the subject not only in a state in which the subject stands up (standing state) but also in a state in which the subject sits on, for example, a chair (including a wheelchair) (sitting state).

As illustrated in FIG. 2, the mammography apparatus 10 according to this embodiment comprises a control unit 20, a storage unit 22, an interface (I/F) unit 24, an operation unit 26, a radiation detector 30, a compression plate driving unit 32, a compression plate 34, and a radiation emitting unit 36. The control unit 20, the storage unit 22, the I/F unit 24, the operation unit 26, the radiation detector 30, the compression plate driving unit 32, and the radiation emitting unit 36 are connected to each other through a bus 39, such as a system bus or a control bus, such that they can transmit and receive various kinds of information.

The control unit 20 according to this embodiment controls the overall operation of the mammography apparatus 10 under the control of the console 12. The control unit 20 comprises a central processing unit (CPU) 20A, a read only memory (ROM) 20B, and a random access memory (RAM) 20C. For example, various programs including an imaging processing program 21 which is executed by the CPU 20A and is for control related to the capture of a radiographic image are stored in the ROM 20B in advance. The RAM 20C temporarily stores various kinds of data.

The radiation detector 30 detects the radiation R transmitted through the breast which is the object. As illustrated in FIG. 3, the radiation detector 30 is provided in an imaging table 40. In the mammography apparatus 10 according to this embodiment, in a case in which imaging is performed, the breast of the subject is positioned on an imaging surface 40A of the imaging table 40 by a user such as a doctor or a radiology technician. For example, the imaging surface 40A with which the breast of the subject comes into contact is made of carbon in terms of the transmission and intensity of the radiation R.

The radiation detector 30 detects the radiation R transmitted through the breast of the subject and the imaging table 40, generates a radiographic image on the basis of the detected radiation R, and outputs image data indicating the generated radiographic image. The type of the radiation detector 30 according to this embodiment is not particularly limited. For example, the radiation detector 30 may be an indirect-conversion-type radiation detector that converts the radiation R into light and converts the converted light into charge or a direct-conversion-type radiation detector that directly converts the radiation R into charge.

For example, the image data of the radiographic image captured by the radiation detector 30 and various other kinds of information are stored in the storage unit 22. Examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 30 in the mammography apparatus 10 is transmitted to the console 12 through the I/F unit 24 by wireless communication or wired communication.

The operation unit 26 is provided as a plurality of switches in, for example, the imaging table 40 of the mammography apparatus 10. In addition, the operation unit 26 may be provided as a touch panel switch or may be provided as a foot switch that is operated by the user's feet.

The radiation emitting unit 36 comprises a visible light source 37V, a radiation source 37R, and a collimator 38. As illustrated in FIG. 3, the radiation emitting unit 36 is provided in an arm portion 42 together with the imaging table 40 and a compression unit 46. In addition, as illustrated in FIG. 3, the mammography apparatus 10 according to this embodiment comprises the arm portion 42, a base 44, and a shaft portion 45. The arm portion 42 is supported by the base 44 so as to be movable in the up-down direction (Z-axis direction). The shaft portion 45 connects the arm portion 42 to the base 44. The arm portion 42 can be relatively rotated with respect to the base 44, using the shaft portion 45 as a rotation axis.

As illustrated in FIG. 3, the radiation emitting unit 36 further comprises a mirror 48 and a filter 49. In a case in which a tube voltage is applied to the radiation source 37R, the radiation source 37R generates the radiation R and emits the generated radiation R to the imaging table 40. The filter 49 is made of a material, such as molybdenum (Mo) or rhodium (Rh), and selectively transmits a desired wavelength component among a plurality of wavelength components included in the radiation R generated by the radiation source 37R.

In a case in which a voltage is applied to the visible light source 37V, the visible light source 37V is turned on, generates visible light V, and emits the generated visible light V. For example, in the mammography apparatus 10 according to this embodiment, the visible light source 37V is provided outside an irradiation field 102 (see FIG. 4) of the radiation R.

The mirror 48 reflects the visible light V emitted from the visible light source 37V to the imaging surface 40A of the imaging table 40 and the irradiation field 102 which becomes a region irradiated with the radiation R is displayed by the reflected visible light V. In the mammography apparatus 10 according to this embodiment, a region of the mammary gland (which will be described in detail below; hereinafter, referred to as a "mammary gland region") of the breast compressed by the compression plate 34 is displayed on a surface of the compression plate 34 (a surface which does not come into contact with the breast) which is close to the radiation emitting unit 36 by the visible light V. In addition, the mirror 48 transmits the radiation R emitted from the radiation source 37R.

Figure 4:
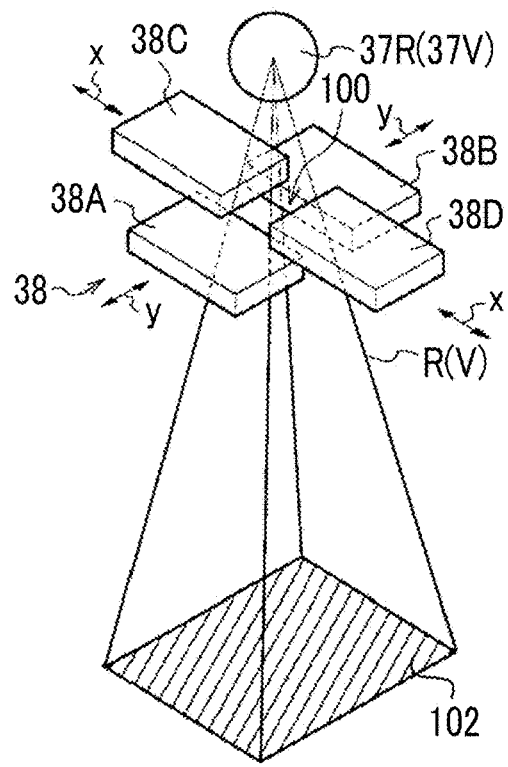
FIG. 4 is a perspective view illustrating an example of the configuration of a collimator according to the first embodiment.

The collimator 38 limits the irradiation field 102 of the radiation R and the visible light V. As illustrated in FIG. 3, the collimator 38 is provided between the mirror 48 and the imaging table 40. FIG. 4 is a perspective view illustrating an example of the configuration of the collimator 38 according to this embodiment. As illustrated in FIG. 4, for example, the collimator 38 according to this embodiment includes four blades 38A, 38B, 38C, and 38D. Each of the blades 38A to 38D is a plate member which has a rectangular shape in a plan view and is made of a material that shields the radiation R, such as lead or tungsten. In the collimator 38, one side surface of the blade 38A faces one side surface of the blade 38B and one side surface of the blade 38C faces one side surface of the blade 38D. In addition, in the collimator 38, an opening portion 100 having a rectangular shape in a plan view is formed by the side surfaces of the blades 38A to 38D which face each other.

In the collimator 38, each of the blades 38A to 38D is moved by a driving unit (not illustrated), such as a motor. The blade 38A and the blade 38B can be moved in the y direction of FIG. 4 and the blade 38C and the blade 38D can be moved in the x direction of FIG. 4 which intersects the y direction. In the collimator 38 according to this embodiment, the movable range of each of the blades 38A to 38D is from a state in which the leading ends of the blades facing each other are in contact with each other, that is, the entire opening portion 100 is closed to a state in which the opening portion 100 is maintained in a rectangular shape in a plan view and has the maximum area. The size of the irradiation field 102 is a shape and size (area) corresponding to the shape and size (area) of the opening portion 100.

As illustrated in FIG. 3, the compression plate 34 and the compression plate driving unit 32 are provided in the compression unit 46. Each of the compression unit 46 and the arm portion 42 can be relatively rotated with respect to the base 44, using the shaft portion 45 as a rotation axis. In this embodiment, gears (not illustrated) are provided in each of the shaft portion 45, the arm portion 42, and the compression unit 46. Each gear is switched between an engaged state and a disengaged state to connect each of the arm portion 42 and the compression unit 46 to the shaft portion 45. One or both of the arm portion 42 and the compression unit 46 connected to the shaft portion 45 are rotated integrally with the shaft portion 45.

The compression plate 34 according to this embodiment is a plate-shaped compression member and is moved in the up-down direction (Z-axis direction) by the compression plate driving unit 32 to compress the breast of the subject against the imaging table 40. As illustrated in FIG. 3, for the movement direction of the compression plate 34, the direction in which the breast is compressed, that is, the direction in which the compression plate 34 becomes closer to the imaging surface 40A is referred to as a "compression direction" and the direction in which the compression of the breast is released, that is, the direction in which the compression plate 34 becomes closer to the radiation emitting unit 36 is referred to as a "decompression direction".

It is preferable that the compression plate 34 is optically transparent in order to check positioning or a compressed state in the compression of the breast. In addition, the compression plate 34 is made of a material having high transmittance for the radiation R. It is desirable that the compression plate 34 is made of a material that facilitates the transmission of ultrasonic waves from an ultrasound probe 65 (see FIG. 6, which will be described in detail below) of the ultrasonography apparatus 16. Examples of the material forming the compression plate 34 include resins such as polymethylpentene, polycarbonate, acrylic, and polyethylene terephthalate. In particular, polymethylpentene is suitable as the material forming the compression plate 34 since it has low rigidity, high elasticity, and high flexibility and has suitable values for acoustic impedance that affects the reflectance of ultrasonic waves and an attenuation coefficient that affects the attenuation of ultrasonic waves. The member forming the compression plate 34 is not limited to this embodiment. For example, the member forming the compression plate 34 may be a film-like member.

The console 12 according to this embodiment has a function of controlling the mammography apparatus 10 using, for example, an imaging order and various kinds of information acquired from a radiology information system (RIS) 5 through a wireless communication local area network (LAN) and commands input by the user through an operation unit 56.

For example, the console 12 according to this embodiment is a server computer. As illustrated in FIG. 2, the console 12 comprises a control unit 50, a storage unit 52, an I/F unit 54, the operation unit 56, and a display unit 58. The control unit 50, the storage unit 52, the I/F unit 54, operation unit 56, and the display unit 58 are connected to each other through a bus 59, such as a system bus or a control bus, such that they can transmit and receive various kinds of information. The console 12 according to this embodiment is an example of a control device according to the present disclosure.

The control unit 50 according to this embodiment controls the overall operation of the console 12. The control unit 50 comprises a CPU 50A, a ROM 50B, and a RAM 50C. For example, various programs including a control processing program 51 (which will be described below) executed by the CPU 50A are stored in the ROM 50B in advance. The RAM 50C temporarily stores various kinds of data. The control processing program 51 according to this embodiment is an example of a control program according to the present disclosure.

For example, the image data of the radiographic image captured by the mammography apparatus 10 and various other kinds of information are stored in the storage unit 52. An HDD or an SSD is given as an example of the storage unit 52.

The operation unit 56 is used by the user to input, for example, commands which are related to the capture of a radiographic image and include a command to emit the radiation R or various kinds of information. Therefore, the operation unit 56 according to this embodiment includes at least an irradiation command button that is pressed by the user to input a command to emit the radiation R. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information to and from the mammography apparatus 10, the RIS 5, and the image storage system 18 using wireless communication or wired communication. In the radiography system 2 according to this embodiment, the console 12 receives the image data of the radiographic image captured by the mammography apparatus 10 from the mammography apparatus 10 through the I/F unit 54, using wireless communication or wired communication.

Figure 5:
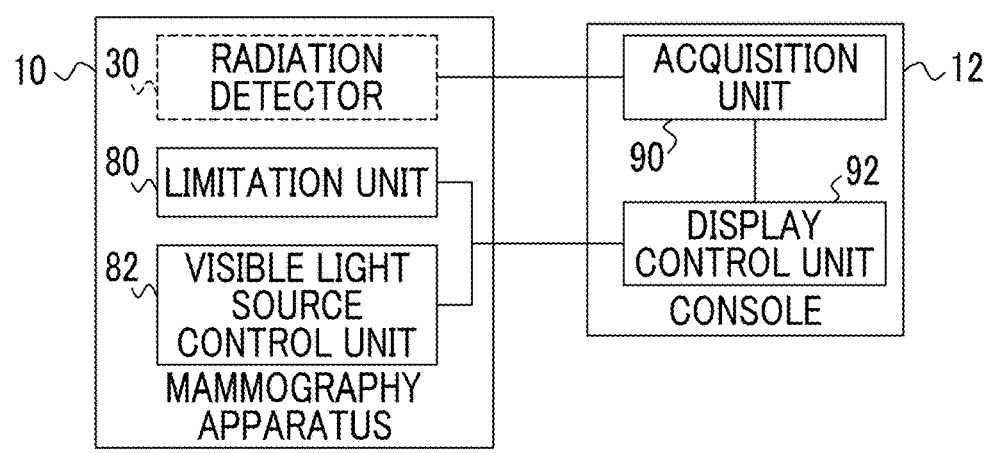
FIG. 5 is a functional block diagram illustrating an example of the function of a radiography system according to the first embodiment.

FIG. 5 is a functional block diagram illustrating an example of the configuration of the radiography system 2 according to this embodiment. As illustrated in FIG. 5, the console 12 according to this embodiment comprises an acquisition unit 90 and a display control unit 92. For example, in the console 12 according to this embodiment, the CPU 50A of the control unit 50 executes the control processing program 51 stored in the ROM 50B such that the control unit 50 functions as the acquisition unit 90 and the display control unit 92.

The acquisition unit 90 of the console 12 acquires region information indicating the mammary gland region of the breast on the basis of the radiographic image captured by the radiation detector 30 of the mammography apparatus 10. For example, the acquisition unit 90 according to this embodiment derives the mammary gland region on the basis of the radiographic image input from the mammography apparatus 10 and outputs region information indicating the derived mammary gland region. A method for deriving the mammary gland region is not particularly limited. For example, the acquisition unit 90 according to this embodiment detects mammary gland tissue pixels corresponding to mammary gland tissues from the radiographic image and derives a region in which the number of detected mammary gland region pixels is equal to or greater than a predetermined value as the mammary gland region. In addition, a method for detecting the mammary gland tissue pixels is not particularly limited. For example, the technique disclosed in JP2010-253245A can be applied. In a case in which the technique disclosed in JP2010-253245A is applied, first, the radiographic image is divided into a breast image and a direct region. Then, a pectoral muscle region is extracted from the breast image. Then, the pectoral muscle region is removed from the breast image. Then, in the breast image from which the pectoral muscle region has been removed, a pixel in which the amount of transmission of the radiation R is equal to or less than a threshold value is detected as the mammary gland tissue region pixel.

The display control unit 92 of the console 12 performs a control process of displaying the mammary gland region on an upper surface 34A of the compression plate 34 that continues to compress the breast from the capture of a radiographic image on the basis of the region information of the mammary gland region output from the acquisition unit 90 so as to be recognizable. In the radiography system 2 according to this embodiment, the collimator 38 of the mammography apparatus 10 limits the irradiation field 102 such that the irradiation field 102 of the visible light V emitted from the visible light source 37V is matched with the mammary gland region. Therefore, for example, the display control unit 92 according to this embodiment transmits information for commanding the turn-on of the visible light source 37V and information related to the irradiation field 102 to the mammography apparatus 10.

As illustrated in FIG. 5, the mammography apparatus 10 according to this embodiment comprises a limitation unit 80 and a visible light source control unit 82. For example, in the mammography apparatus 10 according to this embodiment, the CPU 20A of the control unit 20 executes the imaging processing program 21 stored in the ROM 20B such that the control unit 20 functions as the limitation unit 80 and the visible light source control unit 82.

The limitation unit 80 of the mammography apparatus 10 limits the opening portion 100 for the visible light V using the collimator 38 to limit the irradiation field 102. Specifically, the information related to the irradiation field 102 is input from the display control unit 92 of the console 12 to the limitation unit 80. The limitation unit 80 moves the collimator 38 on the basis of the information related to the irradiation field 102 to define the position and range of the irradiation field 102 of the visible light V, thereby limiting the range in which the radiation R is emitted.

The visible light source control unit 82 of the mammography apparatus 10 controls the turn-on and turn-off the visible light source 37V. Specifically, information for commanding the turn-on of the visible light source 37V is input from the display control unit 92 of the console 12 to the visible light source control unit 82. The visible light source control unit 82 turns on the visible light source 37V on the basis of the input information.

Figure 6:
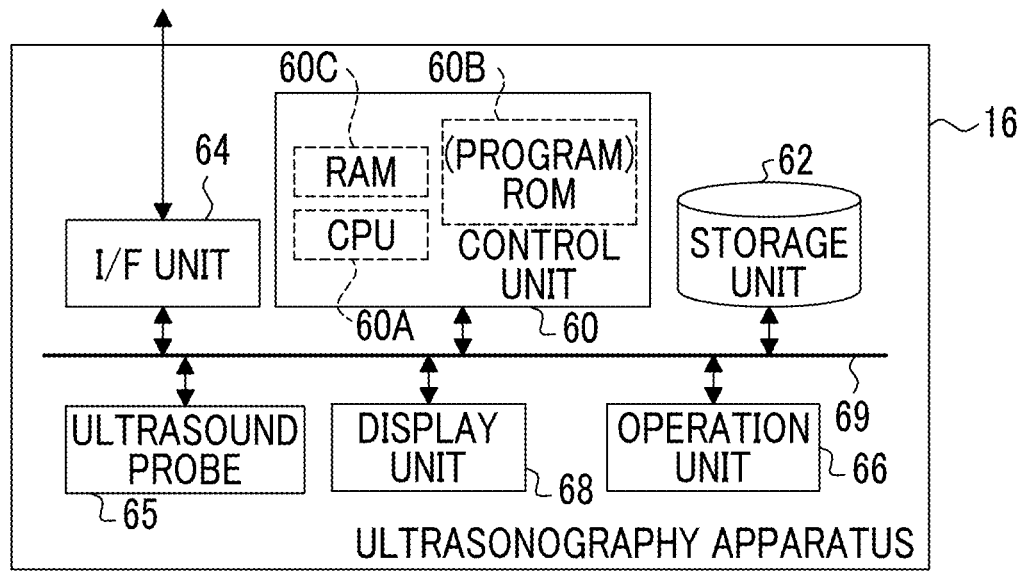
FIG. 6 is a block diagram illustrating an example of the configuration of an ultrasonography apparatus according to the first embodiment.

Next, the configuration of the ultrasonography apparatus 16 will be described. FIG. 6 is a block diagram illustrating an example of the configuration of the ultrasonography apparatus 16. The ultrasonography apparatus 16 is used by the user to capture an ultrasound image of the breast of the subject as the object and is a so-called hand-held ultrasonography apparatus.

As illustrated in FIG. 6, the ultrasonography apparatus 16 comprises a control unit 60, a storage unit 62, an I/F unit 64, the ultrasound probe 65, an operation unit 66, and a display unit 68. The control unit 60, the storage unit 62, the I/F unit 64, the ultrasound probe 65, the operation unit 66, and the display unit 68 are connected to each other through a bus 69, such as a system bus or a control bus, such that they can transmit and receive various kinds of information.

The control unit 60 according to this embodiment controls the overall operation of the ultrasonography apparatus 16. The control unit 60 comprises a CPU 60A, a ROM 60B, and a RAM 60C. For example, various programs executed by the CPU 60A are stored in the ROM 60B in advance. The RAM 60C temporarily stores various kinds of data.

For example, the image data of the captured ultrasound image and various other kinds of information are stored in the storage unit 62. A specific example of the storage unit 62 is an HDD or an SSD.

The ultrasound probe 65 is moved along the upper surface 34A (see FIG. 3, a surface opposite to the surface that comes into contact with the breast of the subject) of the compression plate 34 by the user and scans the breast with ultrasonic waves to acquire an ultrasound image of the breast. Specifically, in a case in which ultrasonography is performed, the ultrasound probe 65 is moved by the user along the upper surface 34A of the compression plate 34 in a state in which an acoustic matching member (not illustrated), such as echo jelly, is applied onto the upper surface 34A of the compression plate 34.

The ultrasound probe 65 comprises a plurality of ultrasound transducers (not illustrated) which are one-dimensionally or two-dimensionally arranged. Each of the ultrasound transducers transmits ultrasonic waves on the basis of an applied driving signal, receives ultrasound echoes, and outputs a received signal.

For example, each of the plurality of ultrasound transducers is a transducer configured by forming electrodes at both ends of a piezoelectric material (piezoelectric body), such as a piezoelectric ceramic typified by lead (Pb) zirconate titanate (PZT) or a polymeric piezoelectric element typified by polyvinylidene difluoride (PVDF). In a case in which a pulsed or continuous wave drive signal is transmitted to apply a voltage to the electrodes of the transducer, the piezoelectric body is expanded and contracted. Pulsed or continuous ultrasonic waves are generated from each transducer by the expansion and contraction and the ultrasonic waves are combined to form an ultrasound beam. Each transducer receives the propagated ultrasonic waves and is then expanded and contracted to generate an electric signal. The electric signal is output as an ultrasound received signal and is input to the main body (not illustrated) of the ultrasonography apparatus 16 through a cable (not illustrated).

The operation unit 66 is used by the user to input, for example, commands or various kinds of information related to the capture of an ultrasound image. The operation unit 66 is not particularly limited. Examples of the operation unit 66 include various switches, a touch panel, a touch pen, and a mouse. The display unit 68 displays, for example, various kinds of information or an ultrasound image corresponding to the received signal from the ultrasound probe 65. In addition, the operation unit 66 and the display unit 68 may be integrated into a touch panel display.

The I/F unit 64 transmits and receives various kinds of information to and from the RIS 5 and the image storage system 18 using wireless communication or wired communication. The image data of the ultrasound image captured by the ultrasonography apparatus 16 is transmitted to the image storage system 18 through the I/F unit 64 by wireless communication or wired communication.

Figure 7:
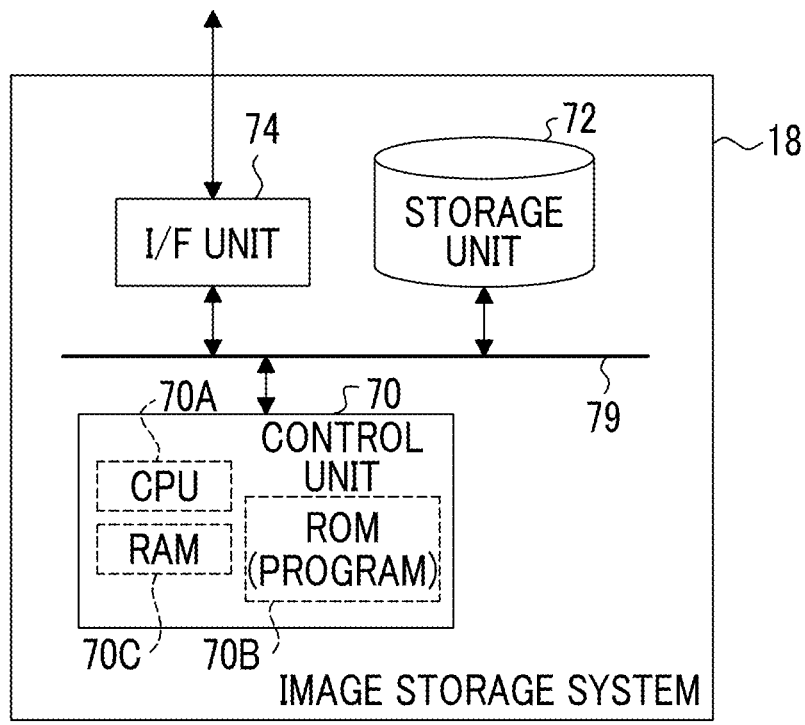
FIG. 7 is a block diagram illustrating an example of the configuration of an image storage system according to the first embodiment.

Next, the configuration of the image storage system 18 will be described. FIG. 7 is a block diagram illustrating an example of the configuration of the image storage system 18. The image storage system 18 stores the image data of the radiographic image captured by the radiography system 2 and the image data of the ultrasound image captured by the ultrasonography apparatus 16. The image storage system 18 extracts an image corresponding to a request from, for example, the console 12, the ultrasonography apparatus 16, and other reading devices (not illustrated) from the stored radiographic images and ultrasound images and transmits the extracted image to the apparatus which is the request source. A specific example of the image storage system 18 is a picture archiving and communication system (PACS).

As illustrated in FIG. 7, the image storage system 18 comprises a control unit 70, a storage unit 72, and an I/F unit 74. The control unit 70, the storage unit 72, and the I/F unit 74 are connected to each other through a bus 79, such as a system bus or a control bus, such that they can transmit and receive various kinds of information.

The control unit 70 according to this embodiment controls the overall operation of the ultrasonography apparatus 16. The control unit 70 comprises a CPU 70A, a ROM 70B, and a RAM 70C. For example, various programs executed by the CPU 70A are stored in the ROM 70B in advance. The RAM 70C temporarily stores various kinds of data.

The storage unit 72 is a so-called database that stores each of the image data of the radiographic image and the image data of the ultrasound image so as to be associated with, for example, an imaging order or information released to the subject.

The I/F unit 74 has a function of transmitting and receiving various kinds of information to and from the console 12 and the ultrasonography apparatus 16 using wireless communication or wired communication.

Figure 8:
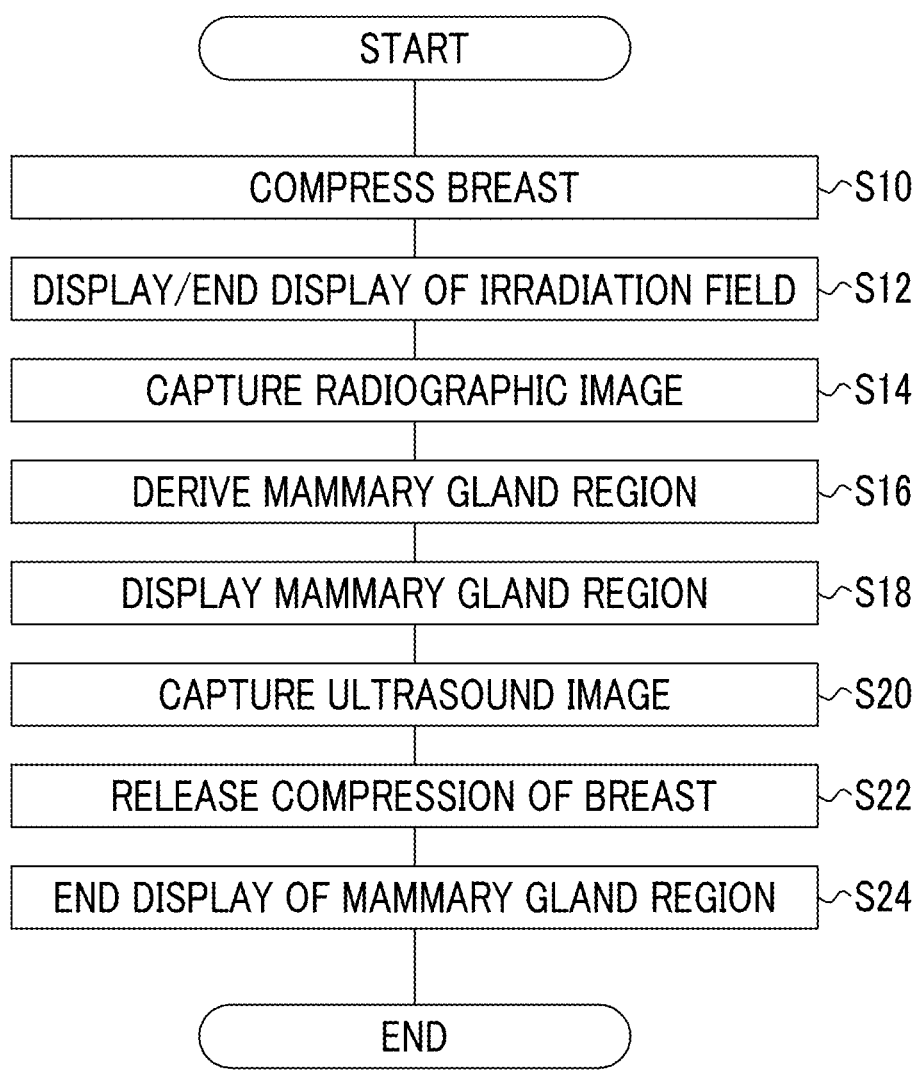
FIG. 8 is a flowchart illustrating an example of the overall flow of imaging in the medical imaging system according to the first embodiment.

Next, the operation of the medical imaging system 1 according to this embodiment will be described with reference to the drawings. First, the overall flow of the imaging operation of the medical imaging system 1 according to this embodiment which captures a radiographic image using the mammography apparatus 10 and captures an ultrasound image using the ultrasonography apparatus 16 will be described. FIG. 8 is a flowchart illustrating an example of the overall flow of the imaging operation of the medical imaging system 1 according to this embodiment.

First, in Step S10, the breast is compressed by the compression plate 34 of the mammography apparatus 10. In a case in which the mammography apparatus 10 according to this embodiment captures a radiographic image, first, the user positions the breast of the subject on the imaging surface 40A of the imaging table 40 of the mammography apparatus 10. In a case in which the positioning is completed, the user inputs a compression command with the operation unit 26. The control unit 20 of the mammography apparatus 10 starts to move the compression plate 34 in the compression direction using the compression plate driving unit 32 in response to the compression command. In a case in which the breast is compressed by the compression plate 34, the breast is fixed between the compression plate 34 and the imaging surface 40A of the imaging table 40 in a state in which the overlap between the mammary gland tissues is developed. In the mammography apparatus 10 according to this embodiment, while the compression command is issued, the compression plate 34 is continuously moved in the compression direction. In other words, in the mammography apparatus 10 according to this embodiment, in a case in which the user stops the compression command through the operation unit 26, the movement of the compression plate 34 is stopped.

Then, in Step S12, the control unit 20 of the mammography apparatus 10 performs control such that the irradiation field 102 based on the imaging order is displayed by the visible light V reflected from the mirror 48 (which will be described in detail below). As such, in the mammography apparatus 10 according to this embodiment, before the radiation R is emitted from the radiation source 37R, the user checks the irradiation field 102 using the visible light V emitted from the visible light source 37V. In a case in which the irradiation field 102 is checked, before a radiographic image is captured, the visible light source 37V is turned off and the display of the irradiation field 102 ends.

Then, in Step S14, the control unit 20 of the mammography apparatus 10 captures a radiographic image of the breast on the basis of the imaging order. Specifically, in a case in which the user presses the irradiation command button included in the operation unit 56 of the console 12, the control unit 20 of the mammography apparatus 10 directs the radiation source 37R to emit the radiation R to the breast compressed by the compression plate 34 under the control of the console 12. Then, the radiation detector 30 generates a radiographic image on the basis of the radiation R transmitted through the breast. The image data of the captured radiographic image is transmitted to the console 12.

Then, in Step S16, the control unit 50 of the console 12 derives the mammary gland region of the breast from the radiographic image acquired from the mammography apparatus 10 (which will be described in detail below). Region information indicating the derived mammary gland region is transmitted to the mammography apparatus 10.

Then, in Step S18, the control unit 20 of the mammography apparatus 10 displays the mammary gland region indicated by the region information on the upper surface 34A of the compression plate 34. Specifically, the limitation unit 80 moves the blades 38A to 38D of the collimator 38 on the basis of the region information to define the position and range of the irradiation field 102 and the visible light source control unit 82 turns on the visible light source 37V.

Then, in Step S20, the user operates the ultrasonography apparatus 16 to capture an ultrasound image of the breast. Specifically, the user applies an acoustic matching member (not illustrated), such as echo jelly, onto the upper surface 34A of the compression plate 34. In this embodiment, the ultrasound image of the breast may not include the entire breast and may include the mammary gland region. Therefore, in a case in which it is determined that the entire breast does not need to be included in the imaging range on the basis of, for example, the imaging order, the acoustic matching member may not cover the entire upper surface 34A and may cover an imaging range including at least the mammary gland region displayed on the upper surface 34A of the compression plate 34.

The user operates the ultrasound probe 65 to scan the imaging range including at least the mammary gland region on the upper surface 34A of the compression plate 34 which is covered by the acoustic matching member with ultrasonic waves, thereby capturing an ultrasound image. The captured ultrasound image is displayed on the display unit 68 of the ultrasonography apparatus 16.

Then, in Step S22, the compression of the breast by the compression plate 34 of the mammography apparatus 10 is released. In the medical imaging system 1 according to this embodiment, in a case in which the capture of the ultrasound image ends, the user inputs a decompression command through the operation unit 26 of the mammography apparatus 10. The control unit 20 of the mammography apparatus 10 moves the compression plate 34 in the decompression direction using the compression plate driving unit 32 in response to the decompression command. The compression plate 34 is moved in the decompression direction to release the compression of the breast. In the mammography apparatus 10 according to this embodiment, while the decompression command is issued, the compression plate 34 is continuously moved in the decompression direction. In other words, in the mammography apparatus 10 according to this embodiment, in a case in which the user stops the decompression command through the operation unit 26, the movement of the compression plate 34 is stopped. The invention is not limited to this embodiment. In a case in which the operation unit 26 includes a decompression button that can move the compression plate 34 to a predetermined decompression position at a stroke in response to one pressing operation of the user, the compression may be released by the decompression button.

As such, in the medical imaging system 1 according to this embodiment, for the period from the start of the capture of a radiographic image to the end of the capture of an ultrasound image, the breast is continuously compressed by the compression plate 34 of the mammography apparatus 10.

Then, in Step S24, the control unit 20 of the mammography apparatus 10 ends the display of the mammary gland region. Then, the entire imaging ends. Specifically, the visible light source control unit 82 turns off the visible light source 37V in response to the decompression command to end the display of the mammary gland region.

Figure 9:
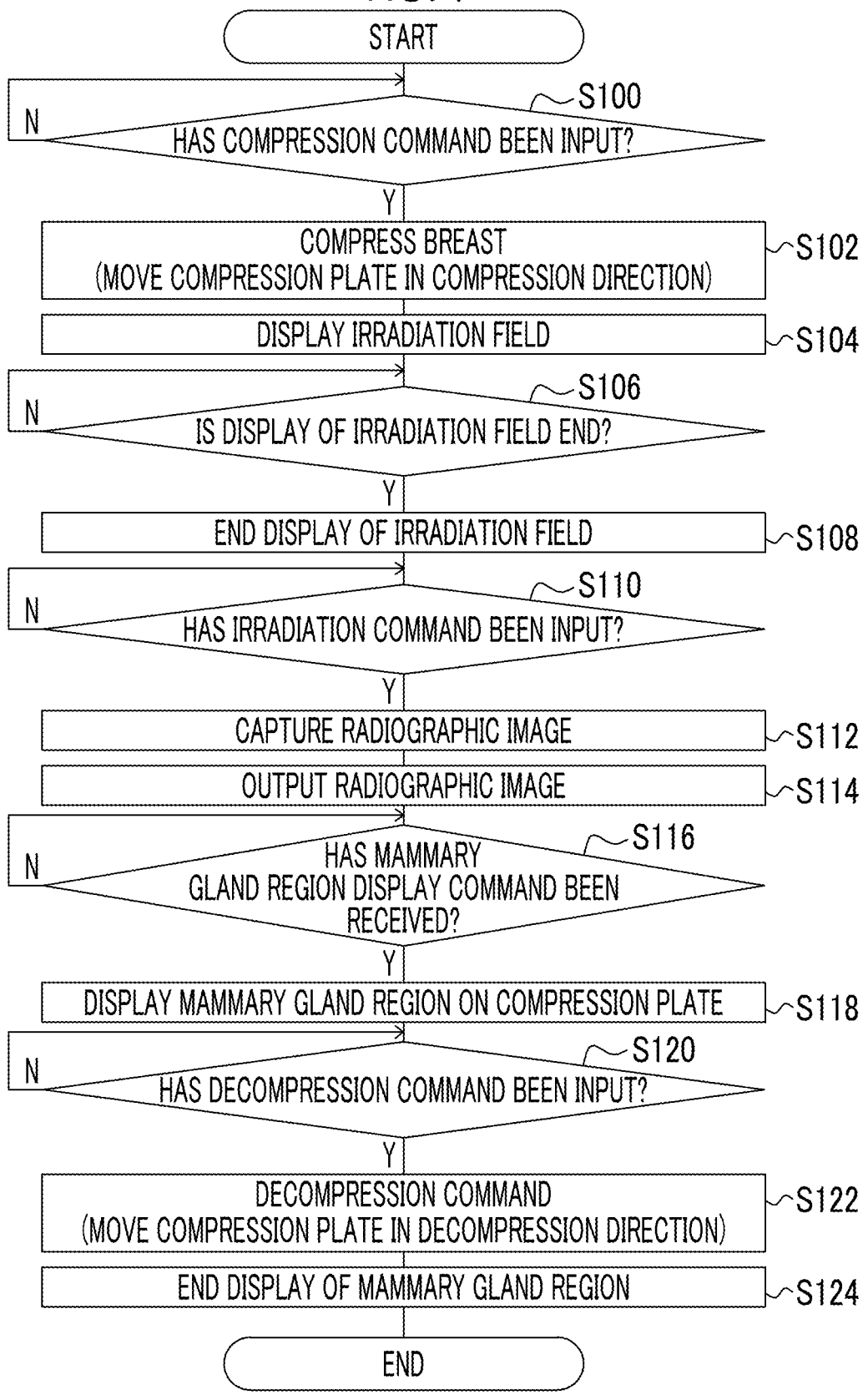
FIG. 9 is a flowchart illustrating an example of the flow of an imaging process of the mammography apparatus according to the first embodiment.

Next, the flow of the imaging operation of the mammography apparatus 10 in the above-mentioned entire imaging will be described. For example, in a case in which the mammography apparatus 10 according to this embodiment receives an imaging order including the capture of both a radiographic image and an ultrasound image and an imaging start command from the console 12, the CPU 20A of the control unit 20 executes the imaging processing program 21 stored in the ROM 20B to perform the imaging process whose example is illustrated in FIG. 9. FIG. 9 is a flowchart illustrating an example of the flow of the imaging process of the mammography apparatus 10 in the entire imaging.

First, in Step S100, the control unit 20 determines whether the user has input a compression command through the operation unit 26. As described in Step S10 (see FIG. 8) of the flow of the entire imaging, in a case in which the breast is compressed, the user inputs the compression command through the operation unit 26. In a case in which the compression command has not been input, the determination result in Step S100 is "No". On the other hand, in a case in which the compression command has been input, the determination result in Step S100 is "Yes" and the process proceeds to Step S102.

In Step S102, the control unit 20 starts to move the compression plate 34 in the compression direction using the compression plate driving unit 32 in response to the compression command such that the breast is compressed between the compression plate 34 and the imaging surface 40A of the imaging table 40 as described in Step S10 (see FIG. 8) of the flow of the entire imaging.

Then, in Step S104, the control unit 20 displays the irradiation field 102 as described in Step S12 (see FIG. 8) of the flow of the entire imaging. Specifically, the limitation unit 80 moves the blades 38A to 38D of the collimator 38 from an initial position on the basis of the imaging order to provide the opening portion 100 corresponding to the desired size of the irradiation field 102. In addition, the visible light source control unit 82 turns on the visible light source 37V.

Then, in Step S106, the control unit 20 determines whether to end the display of the irradiation field 102. The determination result in Step S106 is "No" until the user inputs a command to end the display of the irradiation field 102 through the operation unit 26. On the other hand, in a case in which the display end command is input, the determination result in Step S106 is "Yes" and the process proceeds to Step S108.

In Step S108, the control unit 20 ends the display of the irradiation field 102 as described in Step S12 (see FIG. 8) of the flow of the entire imaging. Specifically, the visible light source control unit 82 turns off the visible light source 37V.

Then, in Step S110, the control unit 20 determines whether a command to emit the radiation R has been input. As described in Step S14 (see FIG. 8) of the flow of the entire imaging, in a case in which the radiation R is emitted, the user inputs an irradiation command through the operation unit 56 of the console 12. In a case in which the irradiation command is input, an irradiation command signal for commanding the emission of the radiation R is transmitted from the console 12 to the mammography apparatus 10. Then, the control unit 20 determines whether the irradiation command has been input on the basis of whether the irradiation command signal has been received from the console 12. The determination result in Step S110 is "No" until the irradiation command signal is received. On the other hand, in a case in which the irradiation command signal is received, the determination result in Step S110 is "Yes" and the process proceeds to Step S112.

In Step S112, the control unit 20 captures a radiographic image as described in Step S14 (see FIG. 8) of the flow of the entire imaging. Specifically, the control unit 20 directs the radiation source 37R of the radiation emitting unit 36 to emit the radiation R to the breast which is the object. The radiation detector 30 generates a radiographic image on the basis of the radiation R transmitted through the breast. In a case in which the capture of the radiographic image ends, the process proceeds to Step S114.

In Step S114, the control unit 20 transmits the image data of the radiographic image generated by the radiation detector 30 to the console 12.

Then, in Step S116, the control unit 20 determines whether a mammary gland region display command (which will be described in detail below) has been received. As described above, the console 12 derives region information indicating the mammary gland region of the breast from the radiographic image captured by the mammography apparatus 10 and outputs the mammary gland region display command to display the derived region information to the mammography apparatus 10. Until the mammary gland region display command transmitted from the console 12 is received, the determination result in Step S116 is "No". On the other hand, in a case in which the mammary gland region display command is received, the determination result in Step S116 is "Yes" and the process proceeds to Step S118.

Figure 10:
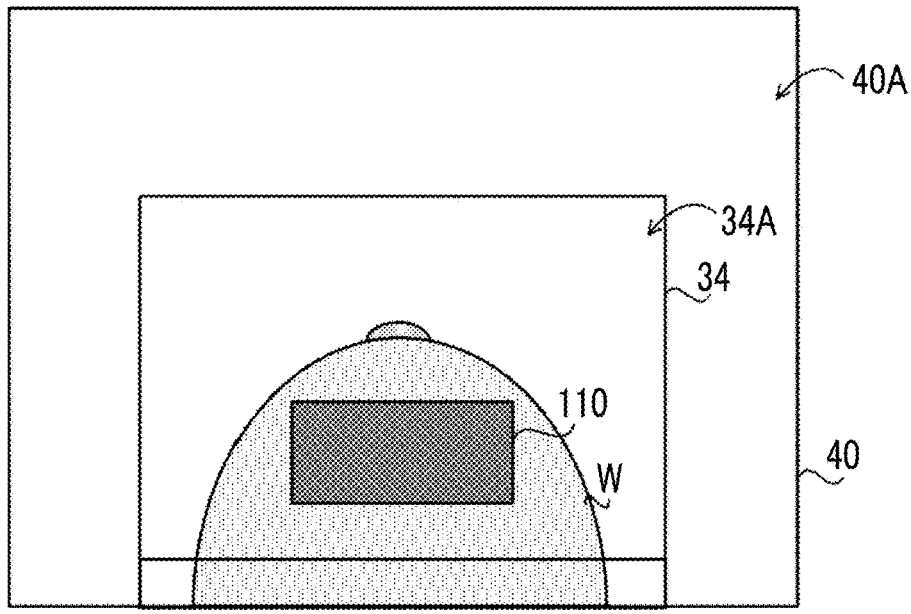
FIG. 10 is a diagram illustrating a state in which an example of a mammary gland region displayed on an upper surface of a compression plate by visible light is viewed from a radiation emitting unit.

In Step S118, the control unit 20 displays the mammary gland region indicated by the region information on the upper surface 34A of the compression plate 34 as described in Step S18 (see FIG. 8) of the flow of the entire imaging. Specifically, the limitation unit 80 moves the blades 38A to 38D of the collimator 38 to adjust the size of the opening portion 100 in response to the mammary gland region display command in order to display the mammary gland region using the irradiation field 102. In addition, the visible light source control unit 82 turns on the visible light source 37V. FIG. 10 illustrates a state in which an example of a mammary gland region 110 displayed on the upper surface 34A of the compression plate 34 by the visible light V is viewed from the radiation emitting unit 36. A method for displaying the mammary gland region 110 may be different from a method for displaying the irradiation field 102 of the radiation R. For example, in a case in which the irradiation field 102 of the radiation R is displayed, the visible light source 37V may be always tuned on. In a case in which the mammary gland region 110 is displayed, the visible light source 37V may be blinked. Further, for example, the emission intensity of the visible light source 37V may be different between a case in which the irradiation field 102 of the radiation R is displayed and a case in which the mammary gland region 110 is displayed such that the intensity of the visible light V is different therebetween.

Then, in Step S120, the control unit 20 determines whether the user has input a decompression command through the operation unit 26. As described in Step S22 (see FIG. 8) of the flow of the entire imaging, in a case in which the compression of the breast is released, the user inputs the decompression command through the operation unit 26. In a case in which the decompression command has not been input, the determination result in Step S120 is "No". On the other hand, in a case in which the decompression command is input, the determination result in Step S120 is "Yes" and the process proceeds to Step S122.

In Step S122, the control unit 20 moves the compression plate 34 in the decompression direction using the compression plate driving unit 32 to release the compression of the breast by the compression plate 34 in response to the decompression command as described in Step S22 (see FIG. 8) of the flow of the entire imaging.

Then, in Step S124, the control unit 20 ends the display of the mammary gland region 110 in response to the decompression command as described in Step S24 (see FIG. 8) of the flow of the entire imaging. Specifically, the visible light source control unit 82 turns off the visible light source 37V in response to the decompression command to end the display of the mammary gland region 110. In this embodiment, the limitation unit 80 moves the blades 38A to 38D of the collimator 38 of the radiation emitting unit 36 to the initial position.

In the mammography apparatus 10 according to this embodiment, in a case in which the display of the mammary gland region 110 ends as described above, the imaging process ends.

Figure 11:
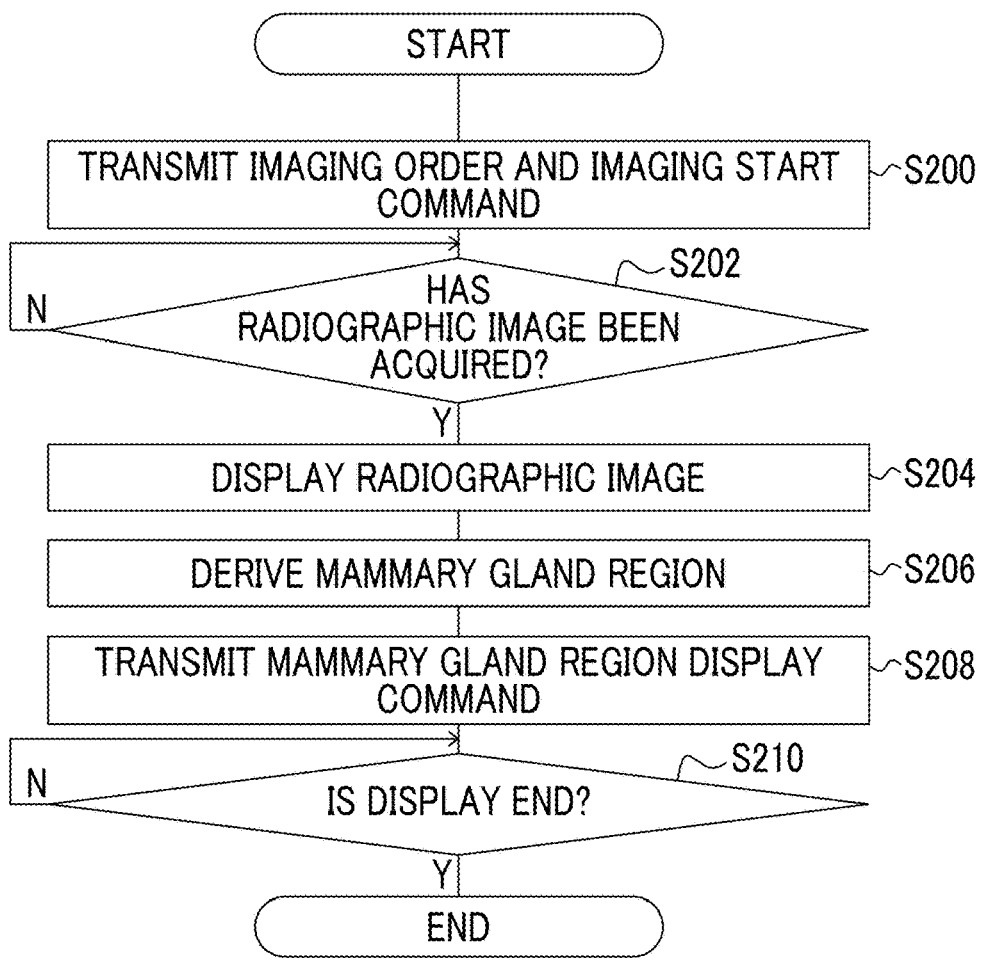
FIG. 11 is a flowchart illustrating an example of the flow of a control process performed by the console according to the first embodiment.

Next, the flow of a control operation of the console 12 in the above-mentioned entire imaging will be described. For example, in a case in which the imaging order acquired from the RIS 5 includes the capture of both a radiographic image and an ultrasound image, the CPU 50A of the control unit 50 in the console 12 according to this embodiment executes the control processing program 51 stored in the ROM 50B to perform the control process whose example is illustrated in FIG. 11. FIG. 11 is a flowchart illustrating an example of the flow of the control process of the console 12 in the entire imaging.

First, in Step S200, the control unit 20 transmits the imaging order and the imaging command to the mammography apparatus 10.

Then, in Step S202, the control unit 20 determines whether a radiographic image has been acquired from the mammography apparatus 10. The determination result in Step S202 is "No" until the console 12 receives the image data of the radiographic image transmitted from the mammography apparatus 10. On the other hand, in a case in which the image data of the radiographic image is received from the console 12, the determination result in Step S202 is "Yes" and the process proceeds to Step S204.

In Step S204, the control unit 20 displays the radiographic image indicated by the received image data on the display unit 58.

Then, in Step S206, the acquisition unit 90 derives a mammary gland region from the radiographic image. As described above, the acquisition unit 90 detects mammary gland tissue pixels from a breast image of the radiographic image, derives a mammary gland region on the basis of the detected mammary gland tissue pixels, and outputs region information indicating the derived mammary gland region to the display control unit 92.

Then, in Step S208, the display control unit 92 transmits a mammary gland region display command to the mammography apparatus 10. The mammary gland region display command is a command for the mammography apparatus 10 to display the region information derived in Step S206. Specifically, the mammary gland region display command includes information for moving the blades 38A to 38D of the collimator 38 of the mammography apparatus 10 such that the opening portion 100 corresponds to the irradiation field 102 corresponding to the mammary gland region derived in Step S206. In addition, the mammary gland region display command includes a command to turn on the visible light source 37V of the mammography apparatus 10.

In a case in which the display control unit 92 outputs the mammary gland region display command in this step, the mammary gland region is displayed on the upper surface 34A of the compression plate 34 of the mammography apparatus 10 in Step S118 (see FIG. 9) of the imaging process in the mammography apparatus 10 as described above.

Then, in Step S210, the control unit 20 determines whether to end the display of the radiographic image on the display unit 58. The determination result in Step S210 is "No" until the user inputs a command to end the display of the radiographic image through the operation unit 56. On the other hand, in a case in which the display end command is input, the determination result in Step S210 is "Yes" and the control process ends.

Second Embodiment

Hereinafter, a second embodiment will be described in detail. Since the overall configuration (see FIG. 1) of a medical imaging system 1 and the configuration of each of a console 12 and a mammography apparatus 10 (see FIG. 2 and FIG. 3) are the same as those in the first embodiment, the description thereof will not be repeated.

Figure 12:
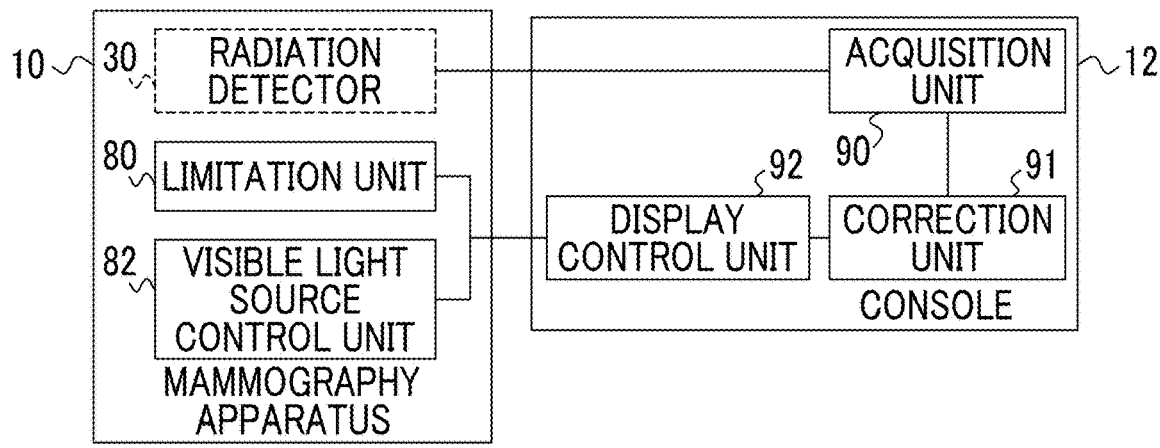
FIG. 12 is a functional block diagram illustrating an example of the function of a radiography system according to a second embodiment.

In this embodiment, since the functions of the console 12 are partially different from the functions of the console 12 according to the first embodiment, the different functions will be described. FIG. 12 is a functional block diagram illustrating an example of the configuration of a radiography system 2 according to this embodiment. As illustrated in FIG. 12, the console 12 according to this embodiment differs from the console 12 (see FIG. 5) according to the first embodiment in that it comprises a correction unit 91. For example, in the console 12 according to this embodiment, the CPU 50A of the control unit 50 executes the control processing program 51 stored in the ROM 50B such that the control unit 50 further functions as the correction unit 91.

Figure 13:
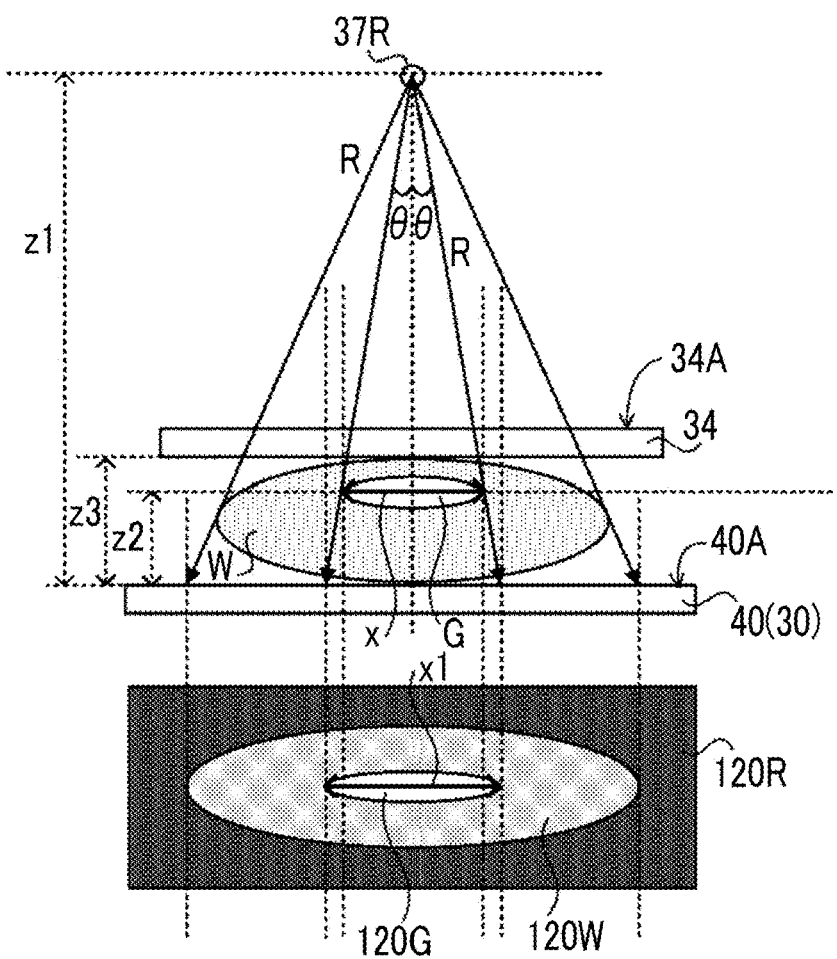
FIG. 13 is a diagram illustrating a difference between the size (width) of a mammary gland image in a radiographic image and the size (width) of the actual mammary gland.

The correction unit 91 corrects the size of the mammary gland region acquired by the acquisition unit 90, that is, the size of a display region in which the mammary gland is displayed. As illustrated in FIG. 13, in some cases, since the radiation R emitted to the breast is obliquely incident, the sizes of a breast image 120W and a mammary gland image 120G in a radiographic image 120R obtained by the radiation detector 30 are different from the actual sizes of a breast W and a mammary gland G. In FIG. 13, for convenience, it is assumed that the imaging surface 40A of the imaging table 40 and a surface (a surface irradiated with the radiation R) of the radiation detector 30 for detecting the radiation R are located at the same position.

It is preferable that the width of the mammary gland region 110 displayed on the upper surface 34A of the compression plate 34 is equal to the actual width x of the mammary gland G. The correction unit 91 according to this embodiment corrects the width x1 of the mammary gland derived from the mammary gland image 120G in the radiographic image 120R to the actual width x of the mammary gland G.

In the example illustrated in FIG. 13, the radiographic image 120R obtained by the radiation detector 30 includes the breast image 120W. In addition, the breast image 120W includes the mammary gland image 120G. In a case in which the distance from the radiation source 37R to the imaging surface 40A, that is, a so-called source-to-image distance (SID) is z1 and the height from the imaging surface 40A to the mammary gland G (for example, the center of gravity of the mammary gland G) is z2, the following Expressions (1) and (2) are established:

$$\tan \theta = (x/2)/(z1-2) \quad (1); \text{ and}$$

$$\tan \theta = (x1/2)/z1 \quad (2).$$

Therefore, the correction unit 91 according to this embodiment corrects the size of the mammary gland region acquired by the acquisition unit 90 by deriving the width x of the mammary gland G as the side (width) of the mammary gland region 110, using the above-mentioned Expressions (1) and (2) and the following Expression (3) obtained for the width x of the mammary gland G:

$$x = x1 \times (z1-z2)/z1 \quad (3).$$

Figure 14:
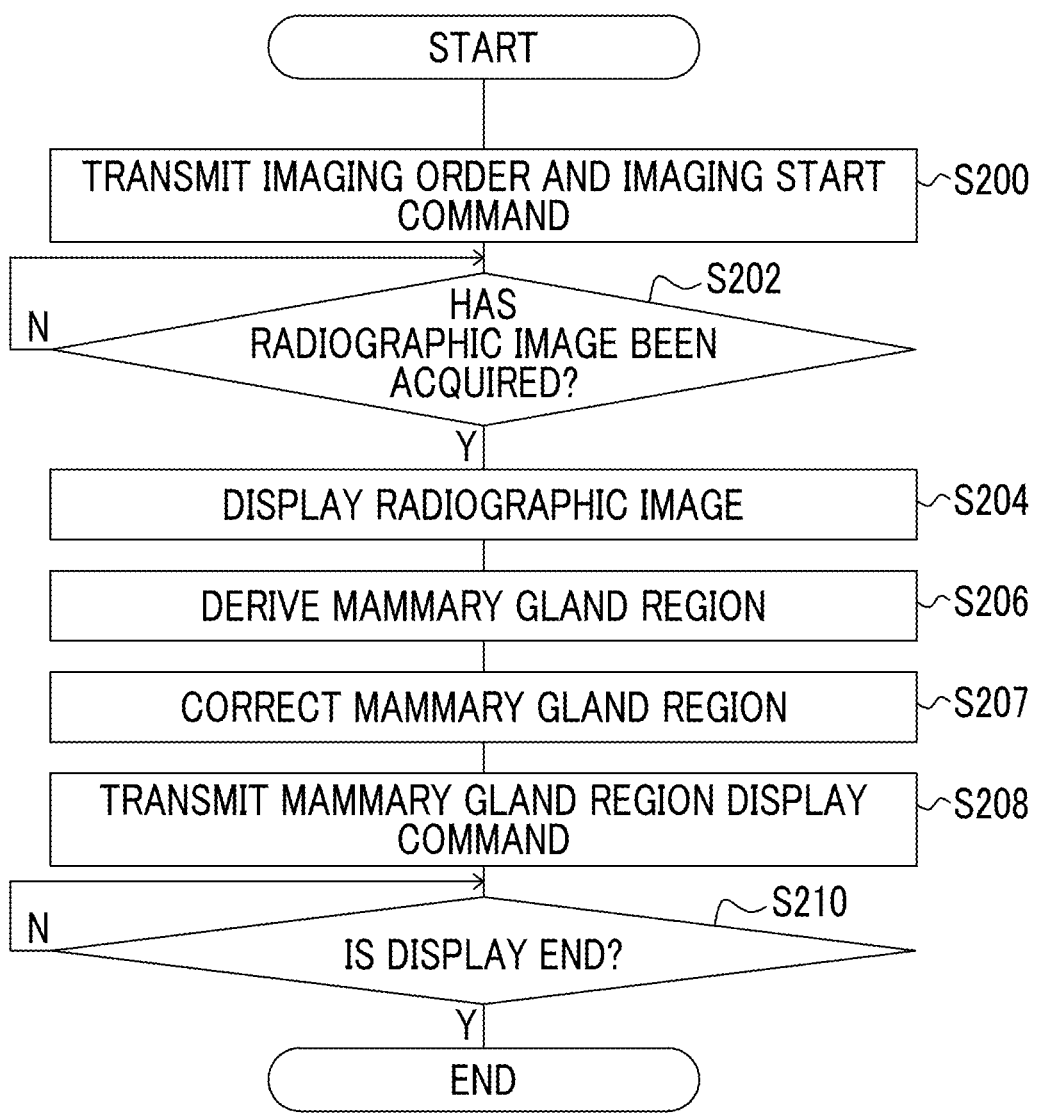
FIG. 14 is a flowchart illustrating an example of the flow of a control process performed by a console according to the second embodiment.

In the operation of the medical imaging system 1 according to this embodiment, since the control operation of the console 12 is partially different from the control operation (see FIG. 11) of the console 12 according to the first embodiment, the control operation of the console 12 according to this embodiment will be described. FIG. 14 is a flowchart illustrating an example of the flow of a control process of the console 12 according to this embodiment. The control process illustrated in FIG. 14 differs from the control process (see FIG. 11) according to the first embodiment in that Step S207 is performed between Step S206 and Step S208.

In Step S207, as described above, the correction unit 91 corrects the size (width) of the mammary gland region 110 derived in Step S206 on the basis of the above-mentioned Expression (3). In the radiography system 2 according to this embodiment, the SID z1 is a value that has been obtained in advance. A method for obtaining the height z2 of the mammary gland G is not particularly limited. For example, the following method can be applied.

For example, in a case in which the capture of a radiographic image by the mammography apparatus 10 (see Step S112 of FIG. 9) is so-called tomosynthesis imaging that captures a plurality of projection images by emitting the radiation R at different irradiation angles and reconstructs a tomographic image from the captured projection images, the height z2 of the mammary gland G may be derived on the basis of the height of the tomographic image including the mammary gland image 120G. For example, as a method simpler than the method using the tomographic image, a method may be used which derives the height z2 on the basis of the thickness of the breast W compressed by the compression plate 34 in the capture of the radiographic image 120R.

A method for obtaining the thickness of the breast W is not particularly limited. For example, the thickness z3 (see FIG. 13) of the breast W compressed by the compression plate 34 may be measured to obtain the thickness of the breast W. For example, the height z3 of the compression plate 34, that is, the distance between the compression plate 34 and the imaging surface 40A may be derived as the thickness z3 of the breast W on the basis of the amount of movement of the compression plate 34 from the initial position.

In some cases, the obtained thickness z3 of the breast W is almost equal to the height z2 of the mammary gland G (z3≈z2). Therefore, for example, the thickness z3 of the breast W may be used as the height z2 of the mammary gland G. In a case in which the height z3 of the compression plate 34 (the distance between the compression plate 34 and the imaging surface 40A) is used as the thickness z3 of the breast W and the thickness z3 of the breast is relatively larger than the height z2 of the mammary gland G, the width x of the mammary gland G derived by the above-mentioned Expression (3) is smaller than the actual width x of the mammary gland G. In this case, for example, a value obtained by multiplying the thickness z3 of the breast by a predetermined coefficient equal to or less than 1 may be used as the height z2 of the mammary gland G.

Therefore, in the next Step S208, the display control unit 92 transmits a mammary gland region display command to display the mammary gland region 110 corrected in Step S207 to the mammography apparatus 10.

Figure 15:
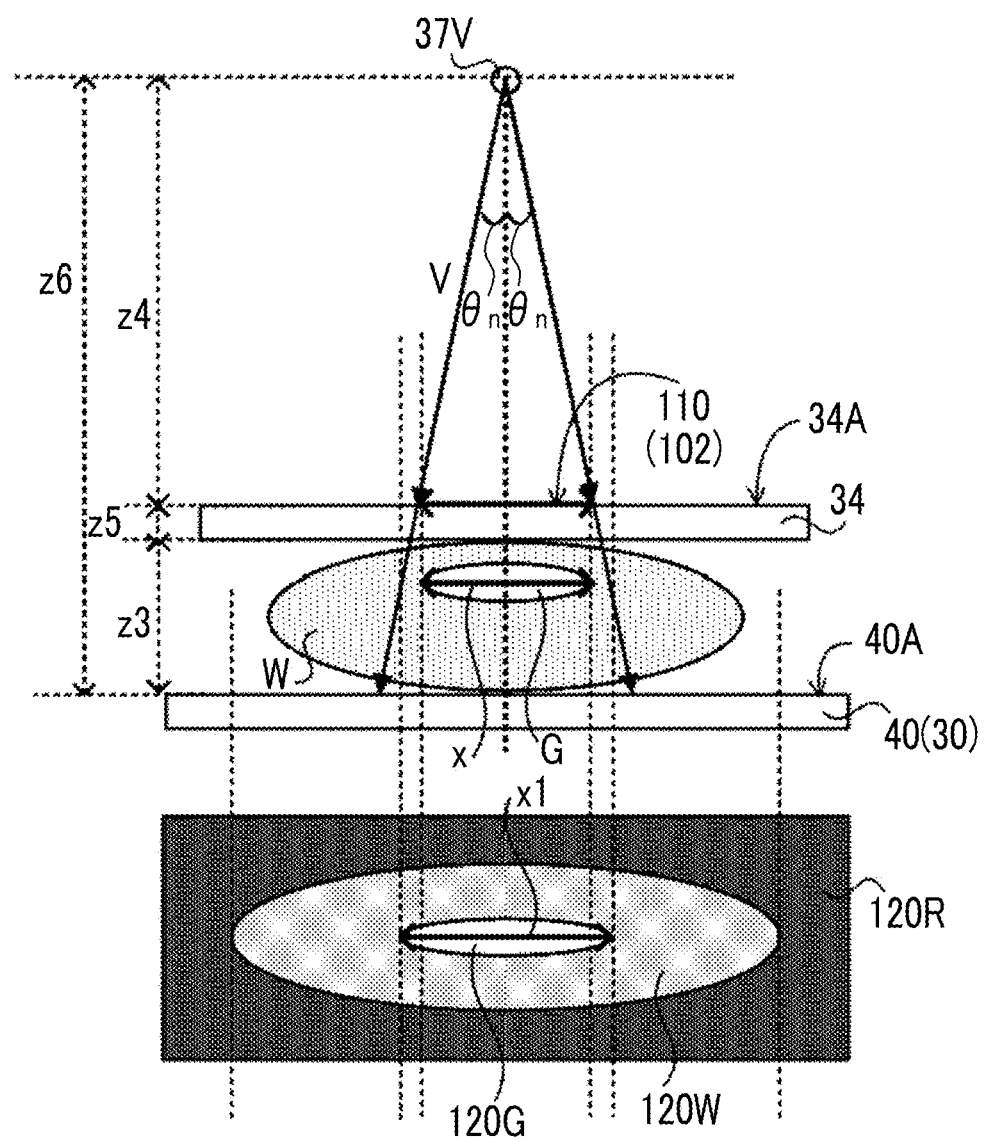
FIG. 15 is a diagram illustrating the display of a mammary gland region corresponding to the size (width) of the actual mammary gland.

As illustrated in FIG. 15, in a case in which the mammary gland region 110 is displayed, the following Expressions (4) and (5) are established for the angle θn of the visible light V emitted from the visible light source 37V:

$$\tan \theta n = x/(2 \times z4) \quad (4); \text{ and}$$

$$\tan \theta n = x/(2 \times (z6 - z3 - z5)) \quad (5).$$

In FIG. 15, the distance from the position of the visible light source 37V, specifically, the reflection position of the mirror 48 to the upper surface 34A of the compression plate 34 is z4, the thickness of the compression plate 34 is z5, and the distance from the position of the visible light source 37V, specifically, the reflection position of the mirror 48 to the imaging surface 40A is z6.

The display control unit 92 according to this embodiment transmits, to the mammography apparatus 10, a mammary gland region display command to move the blades 38A to 38D of the collimator 38 for forming the opening portion 100 corresponding to tan θn obtained by the above-mentioned Expression (4) or Expression (5).

Third Embodiment

Next, a third embodiment will be described in detail. Since the overall configuration (see FIG. 1) of a medical imaging system 1 and the configuration of each of a console 12 and a mammography apparatus 10 (see FIG. 2 and FIG. 3) are the same as those in the first embodiment, the description thereof will not be repeated.

Figure 16:
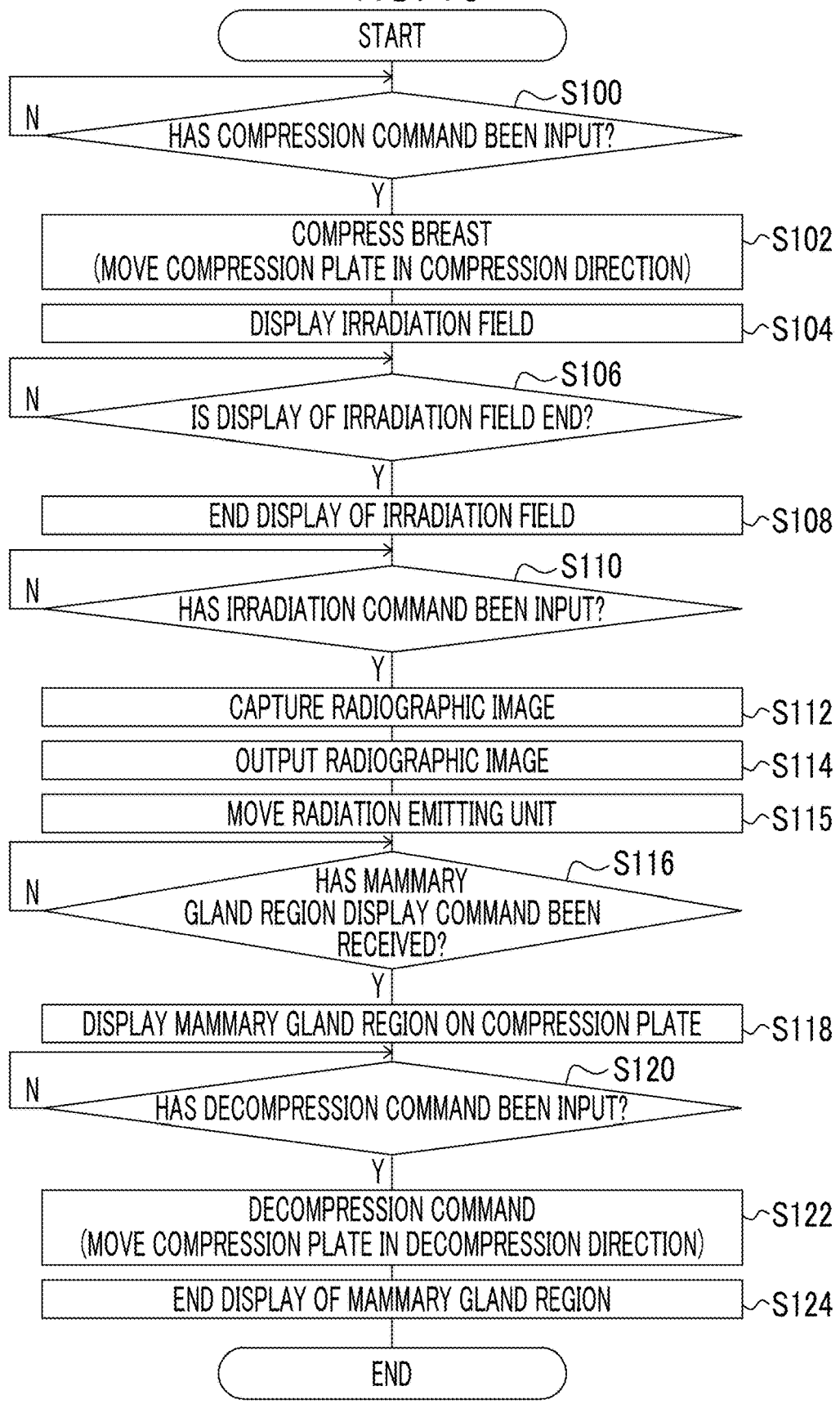
FIG. 16 is a flowchart illustrating an example of the flow of an imaging process of a mammography apparatus according to a third embodiment.

In this embodiment, since an imaging process of the mammography apparatus 10 is partially different from the imaging process (see FIG. 9) of the mammography apparatus 10 according to the first embodiment, the imaging process of the mammography apparatus 10 according to this embodiment will be described. FIG. 16 is a flowchart illustrating an example of the flow of the imaging process of the mammography apparatus 10 according to this embodiment. The imaging process illustrated in FIG. 16 differs from the imaging process (see FIG. 9) according to the first embodiment in that Step S115 is performed between Step S114 and Step S116.

In the capture of an ultrasound image, in some cases, the radiation emitting unit 36 makes it difficult to perform operations with the ultrasound probe 65 or to visually recognize the mammary gland region 110.

Therefore, in the imaging process of the mammography apparatus 10 according to this embodiment, after the capture of a radiographic image ends, the control unit 20 moves the radiation emitting unit 36 to the position where the radiation emitting unit 36 does not hinder the capture of an ultrasound image in Step S115. An example of the position where the radiation emitting unit 36 does not hinder the capture of an ultrasound image is the position of the radiation emitting unit 36 in mediolateral oblique (MLO) imaging.

Figure 17:
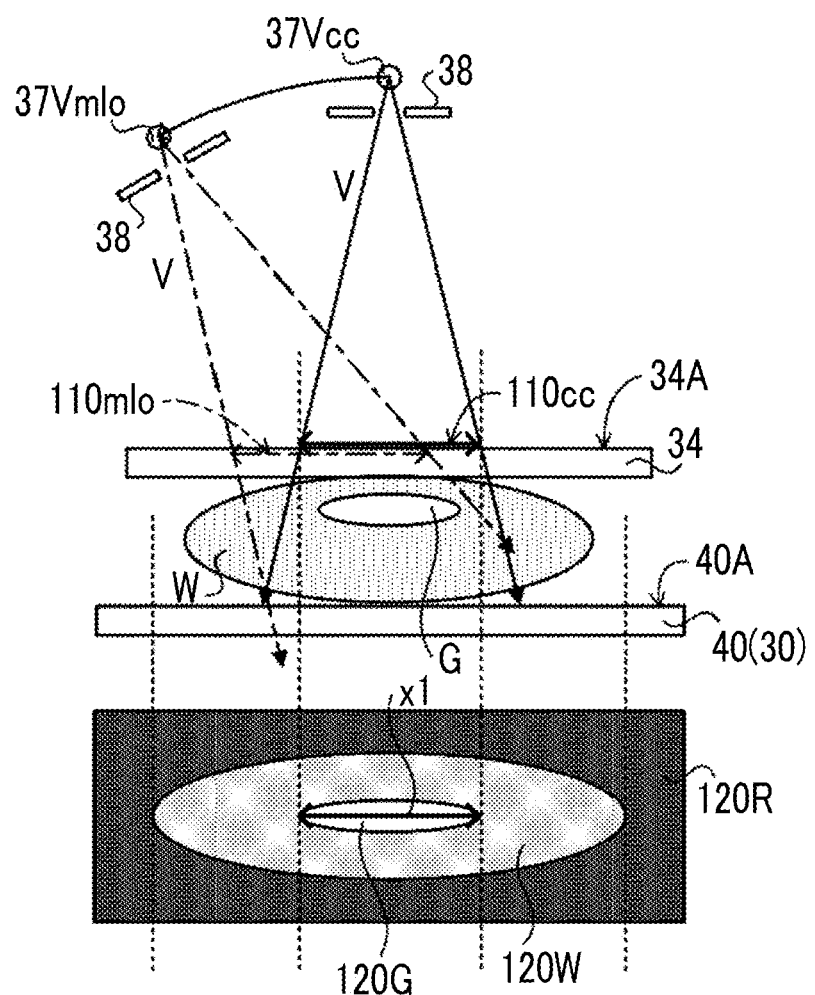
FIG. 17 is a diagram illustrating a case in which an irradiation field on an upper surface of a compression plate, that is, the display position of a mammary gland region is shifted by the movement of a visible light source.
Figure 18:
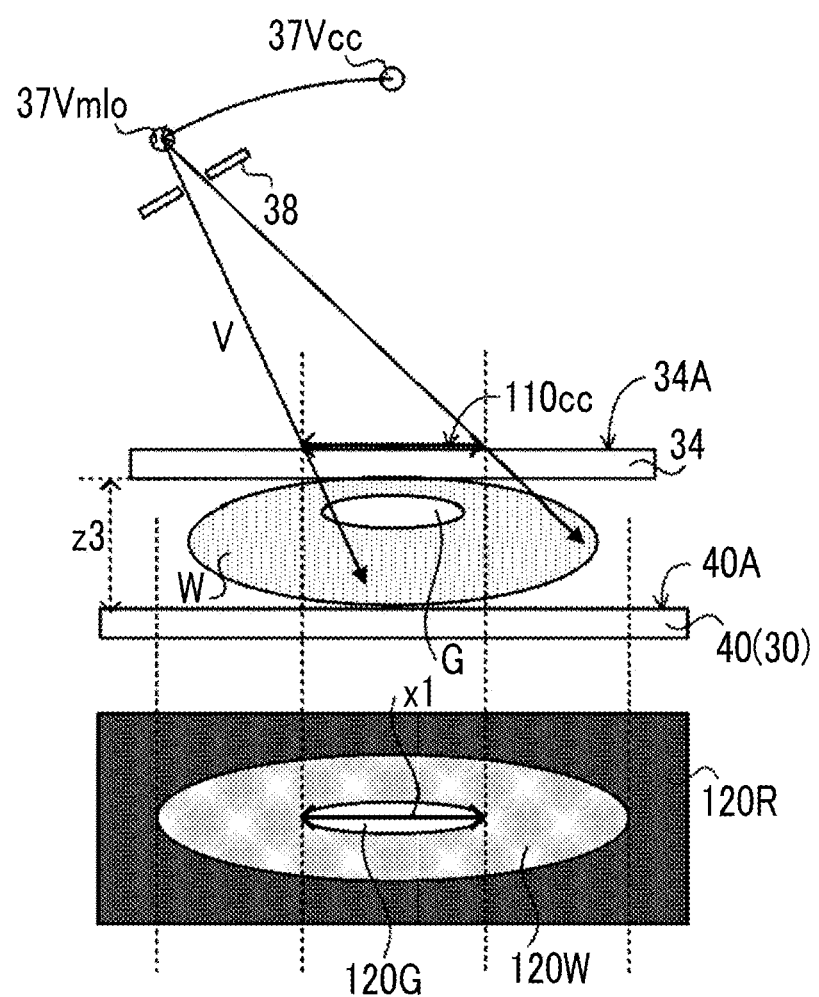
FIG. 18 is a diagram illustrating a state in which the actual mammary gland region is displayed on the upper surface of the compression plate in a case in which the visible light source is moved.

In a case in which the radiation emitting unit 36 is moved, the visible light source 37V is also moved. Therefore, in some cases, the position of the mammary gland region 110 on the upper surface 34A of the compression plate 34 deviates from the position before the radiation emitting unit 36 is moved. In the example illustrated in FIG. 17, the display position of a mammary gland region 110mlo by a visible light source 37Vmlo at an MLO imaging position deviates from the display position of a mammary gland region 110cc by a visible light source 37Vcc at a craniocaudal (CC) imaging position. In this case, it is preferable that the display control unit 92 performs control to move the collimator 38, specifically, the blades 38A to 38D such that the position of the mammary gland region 110mlo by the visible light source 37Vmlo is matched with the position of the mammary gland region 110cc by the visible light source 37Vcc as illustrated in FIG. 18. The display control unit 92 can derive the amount of movement of the collimator 38 from the height z3 of the compression plate 34 and the inclination angle of the visible light source 37Vmlo.

In other words, it is preferable that the mammary gland region display command issued by the display control unit 92 of the console 12 according to this embodiment includes information for moving the collimator 38, specifically, the collimator 38 (blades 38A to 38D) for displaying the mammary gland region 110cc according to the movement of the radiation emitting unit 36.

As described above, the radiography system 2 according to each of the above-described embodiments comprises the mammography apparatus 10 and the console 12. The mammography apparatus 10 includes the radiation source 37R, the radiation detector 30, and the compression plate 34 that compresses the breast W disposed between the radiation source 37R and the radiation detector 30 and captures the radiographic image 120R of the breast W in the compressed state using the radiation detector 30. The console 12 comprises the acquisition unit 90 that acquires region information indicating the region of the mammary gland G in the breast W on the basis of the radiographic image 120R captured by the mammography apparatus 10 and the display control unit 92 that performs control to display the mammary gland region 110 on the upper surface 34A of the compression plate 34 which continues to compress the breast W from the capture of the radiographic image 120R on the basis of the region information acquired by the acquisition unit 90 such that the mammary gland region can be recognized.

In the above-mentioned configuration, in the radiography system 2 according to each of the above-described embodiments, after the mammography apparatus 10 captures the radiographic image 120R, the mammary gland region 110 is displayed in a state in which the breast W is continuously compressed. According to the radiography system 2 of each of the above-described embodiments, since the compression of the breast W is not released, it is possible to suppress a significant change in the developed state of the mammary gland tissues. Therefore, according to the radiography system 2 of each of the above-described embodiments, it is possible to appropriately display the mammary gland region 110 of the compressed breast W on the upper surface 34A of the compression plate 34 that compresses the breast W.

In the radiography system 2 according to each of the above-described embodiments, since the mammary gland region 110 is appropriately displayed, the user can appropriately set the imaging range (scanning range) of an ultrasound image. In the capture of an ultrasound image, it is possible to set a scanning range corresponding to the mammary gland region 110. Therefore, the imaging range can be narrower than that in a case in which the image of the entire breast W is captured and it is possible to reduce the imaging time. In the radiography system 2 according to each of the above-described embodiments, since the imaging time can be reduced, it is possible to alleviate the pain of the subject caused by the compression of the breast W.

Figure 19:
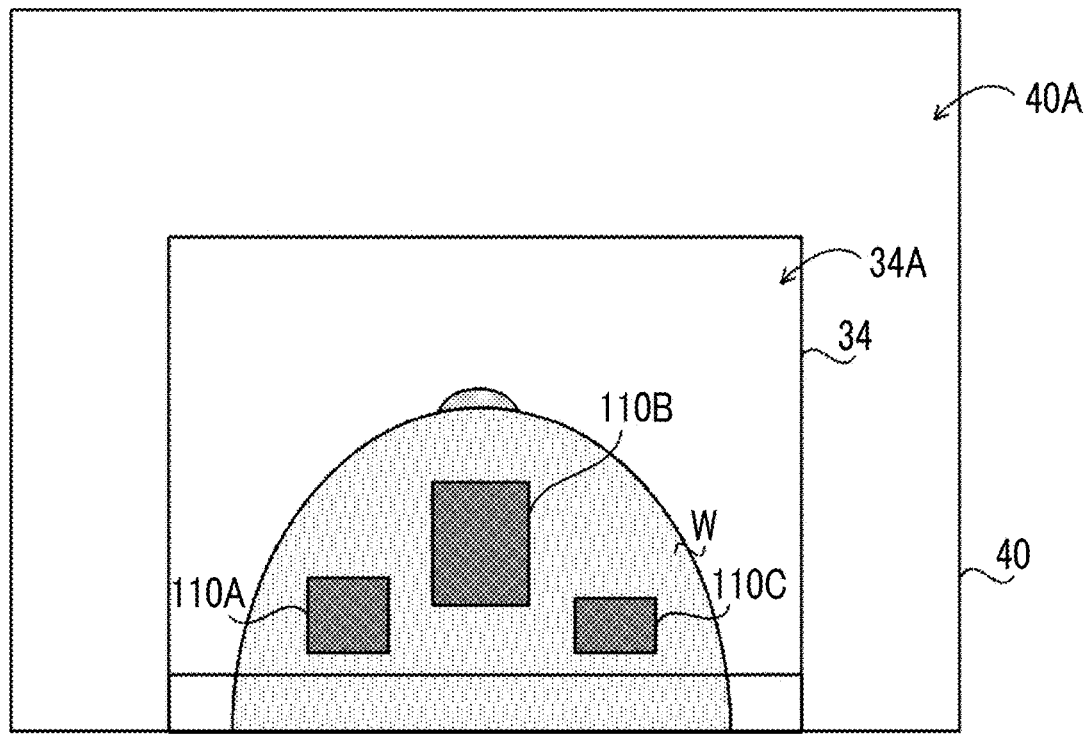
FIG. 19 is a diagram illustrating an example of display in a case in which there are a plurality of mammary gland regions.
Figure 20:
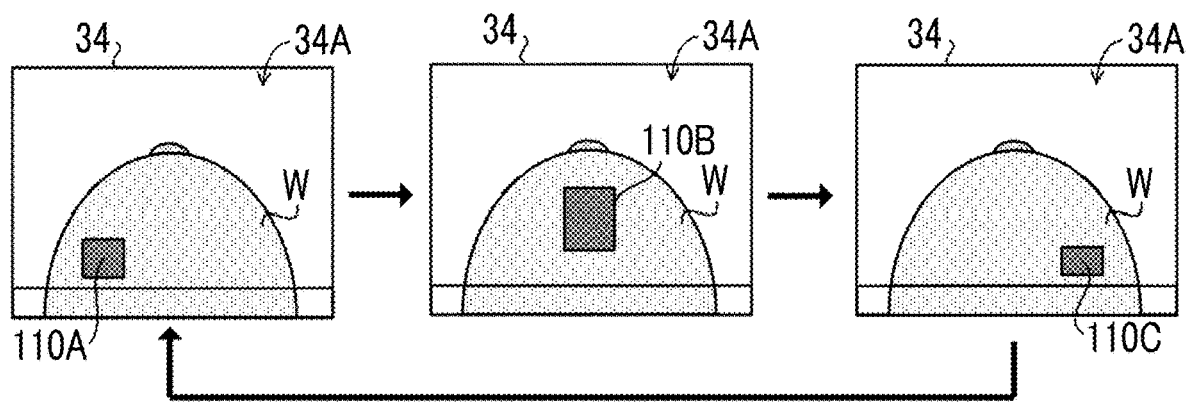
FIG. 20 is a diagram illustrating another example of display in a case in which there are a plurality of mammary gland regions.

In each of the above-described embodiments, the case in which there is one mammary gland region 110 has been described. However, there may be a plurality of mammary gland regions 110. In a case in which there are a plurality of mammary gland regions 110 (three mammary gland regions 110 in FIG. 19 and FIG. 20), mammary gland regions 110A, 110B, and 110C may be displayed on the upper surface 34A of the compression plate 34 at the same time as illustrated in FIG. 19. In addition, as illustrated in FIG. 20, the mammary gland region 110A, the mammary gland region 110B, and the mammary gland region 110C may be sequentially displayed one by one on the upper surface 34A of the compression plate 34. In a case in which the plurality of mammary gland regions 110 (110A, 110B, and 110C) are sequentially displayed, it is preferable that the total number of mammary gland regions 110 is displayed on, for example, the display unit 58 of the console 12 since it is difficult for the user to recognize the total number of mammary gland regions 110.

As such, in a case in which the plurality of mammary gland regions 110 are displayed at the same time, a plurality of visible light sources 37V may be provided or, for example, a liquid crystal filter having a plurality of opening portions may be provided instead of the collimator 38.

Figure 21:
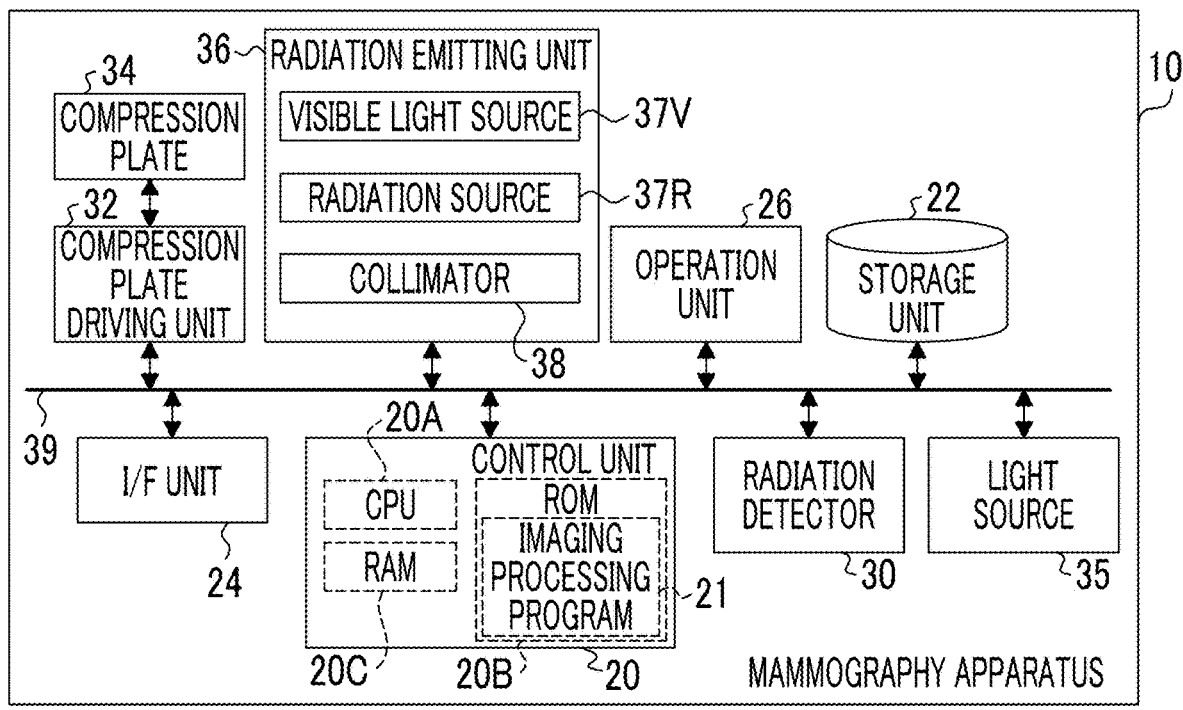
FIG. 21 is a block diagram illustrating another example of the configuration of the mammography apparatus.

In each of the above-described embodiments, the aspect in which the mammary gland region 110 is displayed by the visible light V emitted from the visible light source 37V used to display the irradiation field 102 has been described. However, as illustrated in FIG. 21, the mammography apparatus 10 may be configured to comprise a light source 35 used only for displaying the mammary gland region 110. In this case, it is preferable that at least one of hue, saturation, and brightness is different between visible light emitted from the light source 35 and the visible light V emitted from the visible light source 37V. In addition, instead of the configuration in which the light source 35 is provided in the mammography apparatus 10, a filter (not illustrated) that changes the hue, saturation, and brightness of the visible light V may be provided in the mammography apparatus 10 and the display control unit 92 may control the filter in a case in which the irradiation field 102 is displayed and a case in which the mammary gland region 110 is displayed.

Figure 22:
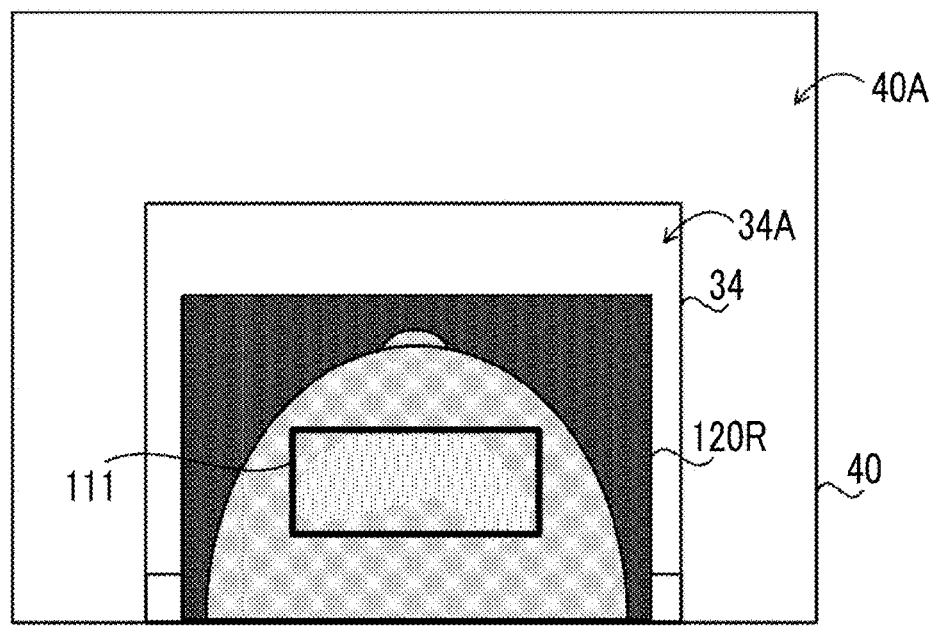
FIG. 22 is a diagram illustrating an example of an aspect in which a radiographic image and a frame indicating a mammary gland region are displayed.

As in an example illustrated in FIG. 22, a radiographic image 120R including a frame 111 indicating the mammary gland region may be displayed on the upper surface 34A of the compression plate 34 by the light source 35.

In each of the above-described embodiments, the aspect in which, in a case in which the compression of the breast W by the compression plate 34 starts in the mammography apparatus 10, the compression of the breast W is maintained without moving the compression plate 34 until the capture of an ultrasound image ends has been described. However, the compressed state of the breast W is not limited to this aspect. The breast W is compressed as described above to develop the overlap of the mammary gland tissues. Therefore, the mammography apparatus 10 according to this embodiment may continuously compress the breast W to such an extent that the overlap state of the mammary gland tissues, that is, the developed state of the mammary gland tissues is not changed, or the amount of change in the overlap state of the mammary gland tissues is within an allowable range even in a case in which it is changed, for example, the size of the mammary gland region 110 is not changed. Therefore, the mammography apparatus 10 may reduce the compression force against the breast W according to the developed state of the mammary gland tissues before an ultrasound image is captured after a radiographic image is captured.

As such, in the medical imaging system 1 according to this embodiment, the breast is continuously compressed by the compression plate 34 of the mammography apparatus 10 for the period from the start of the capture of a radiographic image to the end of the capture of an ultrasound image.

In each of the above-described embodiments, the aspect in which the acquisition unit 90 of the console 12 derives the mammary gland region 110 has been described. However, the acquisition unit 90 may acquire region information indicating the mammary gland region derived by, for example, another apparatus. In this case, for example, the mammary gland region 110 may be derived by the mammography apparatus 10 or an apparatus outside the radiography system 2. In addition, the following configuration may be used: in a case in which the user designates the mammary gland region 110 in the radiographic image displayed on the display unit 58 of the console 12 with the operation unit 56, the acquisition unit 90 acquires region information indicating the mammary gland region 110.

In this embodiment, the aspect in which the mammary gland is the object of interest has been described. However, the object of interest is not limited to the mammary gland. For example, the object of interest may be an implant.

In each of the above-described embodiments, for example, the following various processors can be used as the hardware structure of processing units performing various processes such as the limitation unit 80, the visible light source control unit 82, the acquisition unit 90, the correction unit 91, and the display control unit 92. The various processors include, for example, a programmable logic device (PLD), such as a field-programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (program) to function as various processing units as described above.

One processing unit may be configured by one of the various processors or a combination of two or more processors of the same type or different types (for example, a combination of a plurality of FPGAs or a combination of a CPU and an FPGA). In addition, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). As such, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the imaging processing program 21 is stored (installed) in the ROM 20B in advance and the control processing program 51 is stored (installed) in the ROM 50B in advance has been described. However, the invention is not limited thereto. Each of the imaging processing program 21 and the control processing program 51 may be recorded on a recording medium, such as a compact disk read only memory (CD-ROM), a digital versatile disk read only memory (DVD-ROM), or a universal serial bus (USB) memory, and then provided. In addition, each of the imaging processing program 21 and the control processing program 51 may be downloaded from an external apparatus through the network.

For example, the configurations and operations of the medical imaging system 1 and radiography system 2 described in each of the above-described embodiments are illustrative and may be changed according to the situation, without departing from the scope and spirit of the invention. In addition, the above-described embodiments may be appropriately combined with each other.

EXPLANATION OF REFERENCES

What is claimed is:

1. A radiography system comprising:
  a mammography apparatus that includes a radiation source, a radiation detector, and a compression member which compresses a breast disposed between the radiation source and the radiation detector and captures a radiographic image of the breast in a compressed state using the radiation detector; and
  a control device including an acquisition unit that acquires region information indicating a region of an object of interest in the breast on the basis of the radiographic image captured by the mammography apparatus and a display control unit that, based on the region information acquired by the acquisition unit, performs control to display the region of the object of interest on the compression member, which continues to compress the breast from the capture of the radiographic image, such that the region of the object of interest displayed on the compression member is recognizable.

2. The radiography system according to claim 1,
  wherein the object of interest is a mammary gland of the breast, and
  the region of the object of interest is a mammary gland region of the breast.

3. The radiography system according to claim 1,
  wherein the acquisition unit derives the region of the object of interest on the basis of the radiographic image.

4. The radiography system according to claim 1, further comprising:
  a correction unit that corrects a size of a display region of the object of interest,
  wherein the display control unit performs control to display the region of the object of interest in the display region corrected by the correction unit.

5. The radiography system according to claim 4,
  wherein the correction unit corrects the size of the display region of the object of interest on the basis of a distance between the radiation source and the radiation detector and a distance between the object of interest and the radiation detector.

6. The radiography system according to claim 4,
  wherein the correction unit corrects the size of the display region of the object of interest on the basis of a distance between the radiation source and the radiation detector and a thickness of the breast.

7. The radiography system according to claim 4,
  wherein the correction unit corrects the size of the display region of the object of interest on the basis of a distance between the radiation source and the radiation detector and a distance between the compression member and the radiation detector.

8. The radiography system according to claim 1,
  wherein the mammography apparatus further comprises a visible light source that emits visible light and a limitation unit that limits an irradiation region of the visible light under the control of the display control unit.

9. The radiography system according to claim 8,
  wherein the mammography apparatus further comprises a collimator that limits an irradiation field of radiation emitted from the radiation source, and
  the limitation unit limits the irradiation region of the visible light using the collimator.

10. The radiography system according to claim 8,
  wherein the display control unit performs control for the limitation unit such that the irradiation region is matched with the region of the object of interest on the basis of a position of the visible light source and an irradiation angle of the visible light.

11. The radiography system according to claim 1,
  wherein the mammography apparatus displays an irradiation field of radiation emitted from the radiation source with visible light, and
  the display control unit performs control to display the region of the object of interest with visible light that is different from the visible light for displaying the irradiation field in any one of hue, brightness, or saturation.

12. The radiography system according to claim 1,
  wherein, in a case in which there are a plurality of regions of the object of interest, the display control unit performs control to sequentially display the plurality of regions of the object of interest.

13. The radiography system according to claim 1,
  wherein the display control unit further performs control to display the radiographic image captured by the mammography apparatus on the compression member.

14. A medical imaging system comprising:
  the radiography system according to claim 1; and
  an ultrasonography apparatus that captures an ultrasound image of the breast compressed by the compression member of the mammography apparatus in the radiography system.

15. A control method performed by a computer, comprising:
  acquiring region information indicating a region of an object of interest in a breast on the basis of a radiographic image captured by a mammography apparatus that includes a radiation source, a radiation detector, and a compression member which compresses the breast disposed between the radiation source and the radiation detector and captures the radiographic image of the breast in a compressed state using the radiation detector; and
  on the basis of the acquired region information, performing control to display the region of the object of interest on the compression member, which continues to compress the breast from the capture of the radiographic image, such that the region of the object of interest displayed on the compression member is recognizable.

16. A non-transitory storage medium storing a program that causes a computer to perform a control processing, the control processing comprising:

acquiring region information indicating a region of an object of interest in a breast on the basis of a radiographic image captured by a mammography apparatus that includes a radiation source, a radiation detector, and a compression member which compresses the breast disposed between the radiation source and the radiation detector and captures the radiographic image of the breast in a compressed state using the radiation detector; and on the basis of the acquired region information, performing control to display the region of the object of interest on the compression member, which continues to compress the breast from the capture of the radiographic image, such that the region of the object of interest displayed on the compression member is recognizable.

* * * * *